United States Patent
Buhr et al.

(10) Patent No.: US 7,307,084 B2
(45) Date of Patent: Dec. 11, 2007

(54) CYCLIC BENZIMIDAZOLES

(75) Inventors: Wilm Buhr, Constance (DE); M. Vittoria Chiesa, Constance (DE); Peter Jan Zimmermann, Radolfzell (DE)

(73) Assignee: Altana Pharma AG, Constance (DE)

( * ) Notice: Subject to any disclaimer, the term of this patent is extended or adjusted under 35 U.S.C. 154(b) by 93 days.

(21) Appl. No.: 10/551,049

(22) PCT Filed: Apr. 2, 2004

(86) PCT No.: PCT/EP2004/050428

§ 371 (c)(1),
(2), (4) Date: Sep. 27, 2005

(87) PCT Pub. No.: WO2004/087701

PCT Pub. Date: Oct. 14, 2004

(65) Prior Publication Data

US 2006/0194968 A1    Aug. 31, 2006

(30) Foreign Application Priority Data

Apr. 4, 2003    (EP) .................................. 03007780

(51) Int. Cl.
A61K 31/4184 (2006.01)
A61K 31/437 (2006.01)
C07D 471/04 (2006.01)
C07D 235/08 (2006.01)

(52) U.S. Cl. .................. 514/293; 514/394; 546/82; 548/302.1

(58) Field of Classification Search ................ 514/293, 514/394; 546/82; 548/302.1
See application file for complete search history.

(56) References Cited

U.S. PATENT DOCUMENTS

2007/0037840 A1 * 2/2007 Buhr .......................... 514/292

FOREIGN PATENT DOCUMENTS

| EP | 0 266 326 B1 | 5/1988 |
| WO | 95/27714 A1 | 10/1995 |
| WO | 97/47603 | 12/1997 |
| WO | 03/014123 A1 | 2/2003 |
| WO | WO 03014123 A1 * | 2/2003 |
| WO | 2004/054984 A1 | 7/2004 |

OTHER PUBLICATIONS

Kaminski, J.J. et al., "Antiulcer Agents. 5. Inhibition of Gastric H+/K+-ATPase by Substituted Imidazo[1,2-a]pyridines and Related Analogues and Its Implication in Modeling the High Affinity Potassium Ion Binding Site of the Gastric Proton Pump Enzyme", J. Med. Chem., vol. 34, pp. 533-541 (1991).

Kaminski, J.J. et al., "Antiulcer Agents. 6. Analysis of the in Vitro Biochemical and in Vivo Gastric Antisecretory Activity of Substituted Imidazo[1,2-a]pyridines and Related Analogues Using Comparative Molecular Field Analysis and Hypothetical Active Site Lattice Methodologies", J. Med. Chem., vol. 40, pp. 427-436 (1997).

Lanas, et al., "Low-dose aspirin and upper gastrointestinal damage: epidemiology, prevention and treatment", Curr. Med. Res. Opin, 23(1); pp. 163-173 (2007).

Rey, et al., "Use of antisecretory drugs among consumers of non-steroidal anti-inflammatory drugs in the general population", Ailment Pharmcol. Ther., vol. 24, pp. 1585-1592 (2006).

Pham, et al., "Acid Suppressive Therapy Use on an Inpatient Internal Medicine Service", Ann. Pharmacother., vol. 40, pp. 1261-1266 (2006).

Lanza, "A Guideline for the Treatment and Prevention of NSAID-induced Ulcers", The American Journal of Gastroenterology, vol. 93, No. 11 (1998).

* cited by examiner

Primary Examiner—Rebecca Anderson
Assistant Examiner—Michael P. Barker
(74) Attorney, Agent, or Firm—The Nath Law Group; Joshua B. Goldberg; Sheldon M. McGee

(57) ABSTRACT

The invention relates to cyclic benzimidazoles of formula 1,

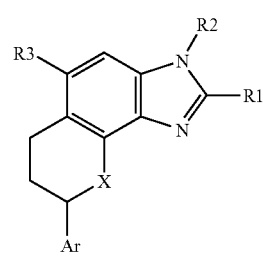

(1)

in which the substituents and symbols have the meanings indicated in the description. The compounds have gastric secretion inhibiting and excellent gastric and intestinal protective action properties.

15 Claims, No Drawings

CYCLIC BENZIMIDAZOLES

TECHNICAL FIELD

The invention relates to novel compounds, which are used in the pharmaceutical industry as active compounds for the production of medicaments.

PRIOR ART

In European patent application 266326 (which corresponds to U.S. Pat. No. 5,106,862), benzimidazole derivatives having a very broad variety of substituents are disclosed, which are said to be active as anti-ulcer agents. In J. Med. Chem. 1991, 34, 533-541 (Kaminski et al.), the inhibition of gastric $H^+/K^+$-ATPase by certain substituted imidazo[1,2-a]pyridines is described. Kaminski et al. describe in a later publication (J. Med. Chem. 1997, 40, 427-436) the results of a detailed analysis of the same and similar imidazo[1,2-a]pyridines. Tricyclic imidazo[1,2-a]pyridines with a specific substitution pattern are described in the International Patent Application WO 95/27714 (Astra AB). In the international Patent Application WO 03/014123 (ALTANA Pharma AG), new imidazo[1,2-]pyridines with a certain substitution pattern are disclosed. In the International Patent Application WO 97/47603 (Astra AB) benzimidazoles with a specific benzyloxy or benzylamino substitution are described.

SUMMARY OF THE INVENTION

The invention relates to condensed benzimidazoles of the formula 1

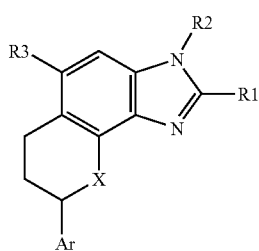

(1)

in which
$R_1$ is hydrogen, halogen, hydroxyl, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl, hydroxy-1-4C-alkyl or mono- or di-1-4C-alkylamino,
R2 is hydrogen, 1-4C-alkyl, 1-4C-alkoxy, 1-4C-alkoxy-1-4C-alkyl, aryl, 3-7C-cycloalkyl, 3-7C-cycloalkyl-1-4C-alkyl, 1-4C-alkoxycarbonyl, mono- or di-1-4C-alkylamino-1-4C-alkylcarbonyl, hydroxy-1-4C-alkyl, fluoro-2-4C-alkyl,
R3 is hydrogen, halogen, fluoro-1-4C-alkyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkoxy-1-4C-alkoxy, 1-4C-alkylcarbonyloxy, 1-4C-alkylcarbonyl-N-1-4-alkylamino, 1-4C-alkoxy-1-4C-alkylcarbonylamino or the group —CO—NR31R32, where
R31 is hydrogen, hydroxyl, 1-7C-alkyl, 3-7C-cycloalkyl, hydroxy-1-4C-alkyl or 1-4C-alkoxy-1-4C-alkyl and R32 is hydrogen, 1-7C-alkyl, 3-7C-cycloalkyl, hydroxy-1-4C-alkyl or 1-4C-alkoxy-1-4C-alkyl,
or where
R31 and R32 together, including the nitrogen atom to which both are bonded, are a pyrrolicino, hydroxypyrrolidino, aziridino, azetidino, piperidino, piperazino, N-1-4C-alkylpiperazino or morpholino group,
X is O (oxygen) or NH and
Ar is a mono- or bicyclic aromatic residue, substituted by R4, R5, R6 and R7, which is selected from the group consisting of phenyl, naphthyl, pyrrolyl, pyrazolyl, imidazolyl, 1,2,3-trazolyl, indolyl, benzimidazolyl, furyl, benzofuryl, thienyl, benzothienyl, thiazolyl, isoxazolyl, pyridinyl, pyrmidinyl, chinolinyl and isochinolinyl,
wherein
R4 is hydrogen, 1-4C-alkyl, hydroxy-1-4C-alkyl, 1-4C-alkoxy, 2-4C-alkenyloxy, 1-4C-alkylcarbonyl, carboxy, 1-4C-alkoxycarbonyl, carboxy-1-4C-alkyl, 1-4C-alkoxycarbonyl-1-4C-alkyl, halogen, hydroxy, aryl, aryl-1-4C-alkyl, aryl-oxy, aryl-1-4C-alkoxy, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sufonyl,
R5 is hydrogen, 1-4C-alkyl, 1-4C-alkoxy, 1-4C-alkoxycarbonyl, halogen, trifluoromethyl or hydroxy,
R6 is hydrogen, 1-4C-alkyl or halogen and
R7 is hydrogen, 1-4C-alkyl or halogen, and wherein
aryl is phenyl or substituted phenyl with one, two or three same or different substituents from the group of 1-4C-alkyl, 1-4C-alkoxy, carboxy, 1-4C-alkoxycarbonyl, halogen, trifluoromethyl, nitro, trifluoromethoxy, hydroxy and cyano, and the salts of these compounds.

Halogen within the meaning of the invention is bromo, chloro and fluoro.

1-4C-Alkyl represents a straight chain or branched alkyl group having 1 to 4 carbon atoms. Examples which may be mentioned are the butyl, isobutyl, sec-butyl, tert-butyl, propyl, isopropyl, ethyl and the methyl group.

3-7C-Cycloalkyl represents cyclopropyl, cyclobutyl, cyclopentyl, cyclohexyl and cycloheptyl, of which cyclopropyl, cyclobutyl and cyclopentyl are preferred.

3-7C-Cycloalkyl-1-4C-alkyl represents one of the aforementioned 1-4C-alkyl groups, which is substituted by one of the aforementioned 3-7C-cycloalkyl groups. Examples which may be mentioned are the cyclopropylmethyl, the cyclohexylmethyl and the cyclohexylethyl group.

1-4C-Alkoxy represents a group, which in addition to the oxygen atom contains one of the aforementioned 1-4C-alkyl groups. Examples which may be mentioned are the butoxy, isobutoxy, sec-butoxy, tert-butoxy, propoxy, isopropoxy and preferably the ethoxy and methoxy group.

1-4C-Alkoxy-1-4C-alkyl represents one of the aforementioned 1-4C-alkyl groups, which is substituted by one of the aforementioned 1-4C-alkoxy groups. Examples which may be mentioned are the methoxymethyl, the methoxyethyl group and the butoxyethyl group.

1-4C-Alkoxycarbonyl (1-4C-alkoxy-CO—) represents a carbonyl group, to which one of the aforementioned 1-4C-alkoxy groups is bonded. Examples which may be mentioned are the methoxycarbonyl ($CH_3O$—C(O)—) and the ethoxycarbonyl group ($CH_2CH_2O$—C(O)—).

2-4C-Alkenyl represents a straight-chain or branched alkenyl group having 2 to 4 carbon atoms. Examples which may be mentioned are the 2-butenyl, 3-butenyl, 1-propenyl and the 2-propenyl group (allyl group).

2-4C-Alkynyl represents a straighten or branched alkynyl group having 2 to 4 carbon atoms. Examples which may be mentioned are the 2-butynyl, 3-butynyl, and preferably the 2-propynyl, group (propargyl group).

Fluoro-1-4C-alkyl represents one of the aforementioned 1-4C-alkyl groups, which is substituted by one or more fluorine atoms. An example which may be mentioned is the trifluoromethyl group.

Hydroxy-1-4C-alkyl represents one of the aforementioned 1-4C-alkyl groups, which is substituted by a hydroxy group. Examples which may be mentioned are the hydroxymethyl, the 2-hydroxyethyl and the 3-hydroxypropyl group. Hydroxy-1-4C-alkyl within the scope of the invention is understood to include 1-4C-alkyl groups with two or more hydroxy groups. Examples which may be mentioned are the 3,4-dihydroxybutyl and in particular the 2,3-dyhydroxypropyl group.

Mono- or di-1-4C-alkylamino represents an amino group, which is substituted by one or by two—identical or different—groups from the aforementioned 1-4C-alkyl groups. Examples which may be mentioned are the dimethylamino, the diethylamino and the diisopropylamino group.

Mono- or di-1-4C-alkylamino-1-4C-alkylcarbonyl represents a 1-4C-alkylcarbonyl group, which is substituted by a mono- or 1-4C-alkylamino groups. Examples, which may be mentioned, are the dimethylamino-methylcarbonyl and the dimethylamino-ethylcarbonyl group.

Fluoro-2-4C-alkyl represents a 2-4C-alkyl group, which is substituted by one or more fluorine atoms. An example which may be mentioned is the 2,2,2-trifluoroethyl group.

1-4C-Alkoxy-1-4C-alkoxy represents one of the aforementioned 1-4C-alkoxy groups, which is substituted by a further 1-4C-alkoxy group. Examples which may be mentioned are the groups 2-(methoxy)ethoxy ($CH_3O-CH_2-O-$) and 2-(ethoxy)ethoxy ($CH_3-CH_2-O-CH_2CH_2-O-$).

1-4C-Alkoxy-1-4C-alkoxy-1-4C-alkyl represents one of the aforementioned 1-4C-alkoxy-1-4C-alkyl groups, which is substituted by one of the aforementioned 1-4C-alkoxy groups. An example which may be mentioned is the group 2-methoxy)ethoxymethyl ($CH_3-O-CH_2-CH_2-O-CH_2$).

Fluoro-1-4C-alkoxy represents one of the aforementioned 1-4C-alkoxy groups, which is completely or mainly substituted by fluorine, "mainly" meaning in this connection that more than half of the hydrogen atoms are replaced by fluorine atoms. Examples of completely or mainly fluoro-substituted 1-4C-alkoxy groups which may be mentioned are the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy group.

Fluoro-1-4C-alkoxy-1-4C-alkyl represents one of the aforementioned 1-4C-alkyl groups, which is substituted by a fluoro-1-4C-alkoxy group. Examples of fluoro-1-4C-alkoxy-1-4C-alkyl groups are the 1,1,2,2-tetrafluoroethoxymethyl, the 2,2,24-trifluoroethoxymethyl, the trifluoromethoxyethyl and the difluoromethoxyethyl group.

1-7C-Alkyl represents a straight-chain or branched alkyl group having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and the methyl group.

Groups Ar which may be mentioned are, for example, the following substituents: 4-acetoxyphenyl, 4-acetamidophenyl, 2-methoxyphenyl, 3-methoxyphenyl, 4-methoxyphenyl, 3-benzyloxyphenyl, 4-benzyloxyphenyl, 3-benzyloxy-4-methoxyphenyl, 4-benzyloxy-3-methoxyphenyl, 3,5-bis (trifluoromethyl)phenyl, 4-butoxyphenyl, 2-chlorophenyl, 3-chlorophenyl, 4-chlorophenyl, 2-chloro-6-fluorophenyl, 3-chloro-fluorophenyl, 2-chloro-5-nitrophenyl, 4chloro-3-nitrophenyl, 3-4chlorophenoxy)phenyl, 2,4-dichlorophenyl, 3,4-difluorophenyl, 2,4-dihydroxyphenyl, 2,6-dimethoxyphenyl, 3,4-dimethoxy-5-hydroxyphenyl, 2,5-dimethylphenyl, 3-ethoxy-4-hydroxyphenyl, 2-fluorophenyl, 4-fluorophenyl, 4-hydroxyphenyl, 2-hydroxy-5-nitrophenyl, 3-methoxy-2-nitrophenyl, 3-nitrophenyl, 2,3,5-trichlorophenyl, 2,4,6-trihydroxyphenyl, 2,3,4-trimethoxyphenyl, 2-hydroxy-1-naphthyl, 2-methoxy-1-naphthyl, 4-methoxy-1-naphthyl, 1-methyl-2-pyrrolyl, 2-pyrrolyl, 3-methyl-2-pyrrolyl, 3,4-dimethyl-2-pyrrolyl, 4-(2-methoxycarbonyl-ethyl)-3-methyl-2-pyrrolyl, 5-ethoxycarbonyl-2,4-dimethyl-3-pyrrolyl, 3,4dibromo-5-ethyl-2-pyrrolyl, 2,5-dimethyl-1-phenyl-3pyrrolyl, 5-carboxy-3-ethyl-4-methyl-2-pyrrolyl, 3,5-dimethyl-2-pyrrolyl, 2,5-dimethyl-1-(4-trifluoromethylphenyl)-3-pyrrolyl, 1-(2,6-dichloro-4-trifluoromethylphenyl)-2-pyrrolyl, 1-(2-nitrobenzyl)-2-pyrrolyl. 1(2-fluorophenyl)-2-pyrrolyl, 1-(4-trifluoromethoxyphenyl)-2-pyrrolyl, 1-(2-nitrobenzyl)-2-pyrrolyl, 1-(4-ethoxycarbonyl)-2,5-dimethyl-3pyrrolyl, 5-chloro-1,3-dimethyl-4-pyrazolyl, 5-chloro-1-methyl-3-trifluoromethyl-4-pyrazolyl, 1-(4-chlorobenzyl)-5-pyrazolyl, 1,3-dimethyl-5-(4-chlorphenoxy)-4-pyrazolyl, 1-methyl-3-trifluomethyl-5-(3-trifluoromethylphenoxy)-4-pyrazolyl, 4-methoxycarbonyl-1-(2,6dichlorophenyl)-5-pyrazolyl, 5-allyloxy-1-methyl-3-trifluoromethyl-4-pyrazolyl, 5-chloro-1-phenyl-3-trifluoromethyl-4-pyrazolyl, 3,5-dimethyl-1-phenyl-4-imidazolyl, 4-bromo-1-methyl-5-imidazolyl, 2-butylimidazolyl, 1-phenyl-1,2,3-triazol-4-yl, 3-indolyl, 4-indolyl, 7-indolyl, 5-methoxy-3-indolyl, 5-benzyloxy-3-indolyl, 1-benzyl-3-indolyl, 2-(4-chlorophenyl)-3-indolyl, 7-benzyloxy-indolyl, 6-benzyloxy-3-indolyl, 2-methyl-5-nitro-3-indolyl, 4,5,6,7-tetrafluoro-3-indolyl, 1(3,5-difluorobenzyl)-3-indolyl, 1-methyl-2-(4-trifluorophenoxy)-3-indolyl, 1-methyl-2-benzimidazolyl, 5-nitro-2-furyl, 5-hydroxymethyl-2-furyl, 2-furyl, 3-furyl, 5(2-nitro-4-trifluoromethylphenyl)-2-furyl, 4-ethoxycarbonyl5-methyl-2-furyl, 5-(2-trifluoromethoxyphenyl)-2-furyl, 5(4-methoxy-2-nitrophenyl)-2-furyl, 4-bromo-2-furyl, 5-dimethylamino-2-furyl, 5-bromo-2-furyl, 5-sulfo-2-furyl, 2-benzofuryl, 2-thienyl, 3-thienyl, 3-methyl-2-thienyl, 4-bromo-2-thienyl, 5-bromo-2-thienyl, 5-nitro-2-thienyl, 5-methyl-2-thienyl, 5-(4-methoxyphenyl)-2-thienyl, 4-methyl-2-thienyl, 3-phenoxy-2-thienyl, 5-carboxy-2-thienyl, 2,5-dichloro-3-thienyl, 3-methoxy-2-thienyl, 2-benzothienyl, 3-methyl-2-benzothienyl, 2-bromo-5-chloro-3-benzothienyl, 2-thiazolyl, 2-amino-4-chloro-5-thiazolyl, 2,4-dichloro-5-thiazolyl, 2-diethylamino-5-thiazolyl, 3-methyl-4-nitro-5-isoxazolyl, 2-pyridyl, 3-pyridyl, 4-pyridyl, 6-methyl-2-pyridyl, 3-hydroxy-5-hydroxymethyl-2-methyl-4-pyridyl, 2,6-dichloro-4-pyridyl, 3-chloro-5-trifluoromethyl-2-pyridyl, 4,6-dimethyl-2-pyridyl, 4(4-chlorophenyl)-pyridyl, 2-chloro-5-methoxycarbonyl-6-methyl-4-phenyl-3-pyridyl, 2-chloro-3pyridyl, 6(3-trifluoromethyl)phenoxy)-3-pyridyl, 2-(4-chlorophenoxy-3-pyridyl, 2,4-dimethoxy-5-pyrimidinyl, 2-quinolinyl, 3-quinolinyl, 4-quinolinyl, 2-chloro-3-quinolinyl, 2-chloro-6-methoxy-3-quinolinyl, 8-hydroxy-2-quinolinyl and 4-isoquinolinyl.

2-4C-Alkenyloxy represents a group, which in addition to the oxygen atom contains one of the above-mentioned 2-4C-alkenyl groups. Examples, which may be mentioned, are the 2-butenyloxy, 3-butenyloxy, 1-propenyloxy and the 2-propenyloxy group (allyloxy group).

1-4C-Alkylcarbonyl represents a group, which in addition to the carbonyl group contains one of the abovementioned 1-4C-alkyl groups. An example which may be mentioned is the acetyl group.

Carboxy-1-4C-alkyl represents a 1-4C-alkyl group which is substituted by a carboxyl group. Examples, which may be mentioned, are the carboxymethyl and the 2-carboxyethyl group.

1-4C-Alkoxycarbonyl-1-4C-alkyl represents a 1-4C-alkyl group, which is substituted by one of the abovementioned 1-4C-alkoxycarbonyl groups. Examples, which may be mentioned, are the Methoxy-carbonylmethyl and the ethoxycarbonylmethyl group.

Aryl-1-4C-alkyl represents one of the aforementioned 1-4C-alkyl groups, which is substituted by one of the abovementioned aryl groups. An exemplary preferred aryl-1-4C-alkyl group is the benzyl group.

Aryl-1-4C-alkoxy represents one of the aforementioned 1-4C-alkoxy groups, which is substituted by one of the abovementioned aryl groups. An exemplary preferred aryl-1-4C-alkoxy group is the benzyloxy group.

1-4C-Alkylcarbonylamino represents an amino group to which a 1-4C-alkylcarbonyl group is bonded. Examples which may be mentioned are the proplonylamino ($C_3H_7C(O)NH$—) and the acetylamino group (acetamido group) ($CH_3C(O)NH$—).

1-4C-Alkoxycarbonylamino represents an amino group, which is substituted by one of the aforementioned 1-4C-alkoxycarbonyl groups. Examples, which may be mentioned, are the ethoxycarbonylamino and the methoxycarbonylamino group.

1-4C-Alkoxy-1-4C-alkoxycarbonyl represents a carbonyl group, to which one of the aforementioned 1-4C-alkoxy-1-4C-alkoxy groups is bonded. Examples which may be mentioned are the 2-(methoxy)ethoxy-carbonyl ($CH_3$—O—$CH_2CH_2$—O—CO—) and the 2-(ethoxy)ethoxycarbonyl group ($CH_3CH_2$—O—$CH_2CH_2$—O—CO—).

1-4C-Alkoxy-1-4C-alkoxycarbonylamino represents an amino group, which is substituted by one of the aforementioned 1-4alkoxy-1-4C-alkoxycarbonyl groups. Examples which may be mentioned are the 2-(methoxy)ethoxycarbonylamino and the 2-(ethoxy)ethoxycarbonylamino group.

Possible salts of compounds of the formula 1—depending on substitution—are especially all acid addition salts. Particular mention may be made of the pharmacologically tolerable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are used in salt preparation—depending on whether a mono- or polybasic acid is concerned and on which salt is desired—in an equimolar quantitative ratio or one differing therefrom.

Pharmacologically intolerable salts, which can initially be obtained, for example, as process products in the production of the compounds according to the invention on the industrial scale, are converted into the pharmacologically tolerable salts by processes known to the person skilled in the art.

It is known to the person skilled in the art that the compounds according to invention and their salts, if, for example, they are isolated in crystalline form, can contain various amounts of solvents. The invention therefore also comprises all solvates and in particular all hydrates of the compounds of the formula 1, and also all solvates and in particular all hydrates of the salts of the compounds of the formula 1.

The compounds of the formula 1 have a chirality center in the 8-position. The invention thus relates to both enantiomers in any desired mixing ratio to another, including the pure enantiomers, which are a preferred subject of the invention.

One aspect of the invention are compounds of formula 1, in which R3 is 1-4C-alkylcarbonyl-N-1-4C-alkylamino and R1, R2, X and Ar have the meanings given above, and the salts of these compounds.

Another aspect of the invention are compounds of formula 1, in which R3 is the group —CO—NR31R32 in which R31 and R32 together, including the nitrogen atom to which both are bonded, are a hydroxy-pyrrolidino group and R1, R2, X and Ar have the meanings given above, and the salts of these compounds.

Yet another aspect of the invention are compounds of formula 1, in which R3 is the group —CO—NR31R32 in which R31 and R32 together, including the nitrogen atom to which both are bonded, are an aziridino group and R1, R2, X and Ar have the meanings given above, and the salts of these compounds.

Yet another aspect of the invention are compounds of formula 1, in which R3 is the group —CO—NR31R32 in which R31 and R32 together, including the nitrogen atom to which both are bonded, are an azetidino group and R1, R2, X and Ar have the meanings given above, and the salts of these compounds.

One embodiment (embodiment a) of the invention are compounds of formula 1, in which R1 is hydrogen, halogen, hydroxyl, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl, hydroxy-1-4C-alkyl or mono- or di-1-4C-alkylamino, R2 is hydrogen, 1-4C-alkyl, 1-4C-alkoxy, 1-4C-alkoxy-1-4C-alkyl, aryl, 3-7C-cycloalkyl, 3-7C-cycloalkyl-1-4C-alkyl, 1-4C-alkoxycarbonyl, mono- or di-1-4C-alkylamino-1-4C-alkylcarbonyl, hydroxy-1-4C-alkyl, fluoro-2-4C-alkyl, R3 is hydrogen, halogen, fluoro-1-4C-alkyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the group —CO—NR31R32, where R31 is hydrogen, hydroxyl, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino, piperazino, N-1-4C-alkylpiperazino or morpholino group, X is O (oxygen) or NH and Ar is a mono- or bicyclic aromatic residue, substituted by R4, R5, R6 and R7, which is selected from the group consisting of phenyl, naphthyl, pyrrolyl, pyrazolyl, imidazolyl, 1,2,3-triazolyl, indolyl, benzimidazolyl, furyl, benzofuryl, thienyl, benzothienyl, thiazolyl, isoxazolyl, pyridinyl, pyrimidinyl, chinolinyl and isochnolinyl,
wherein
R4 is hydrogen, 1-4C-alkyl, hydroxy-1-4C-alkyl, 14C-alkoxy, 2-4C-alkenyloxy, 1-4C-alkylcarbonyl, carboxy, 1-4C-alkoxycarbonyl, carboxy-1-4C-alkyl, 1-4C-alkoxycarbonyl-1-4C-alkyl, halogen, hydroxy, aryl, aryl-1-4C-alkyl, aryl-oxy, aryl-1-4C-alkoxy, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl,
R5 is hydrogen, 1-4C-alkyl, 1-4C-alkoxy, 1-4C-alkoxycarbonyl, halogen, trifluoromethyl or hydroxy,
R6 is hydrogen, 1-4C-alkyl or halogen and
R7 is hydrogen, 1-4C-alkyl or halogen,
and wherein
aryl is phenyl or substituted phenyl with one, two or three same or different substituents from the group of 1-4C-alkyl, 1-4C-alkoxy, carboxy, 1-4C-alkoxycarbonyl, halogen, trifluoromethyl, nitro, trifluoromethoxy, hydroxy and cyano, and the salts of these compounds.

Compounds to be mentioned particularly are those of formula 1, in which
R1 is hydrogen, 1-4C-alkyl, 3-7C-cycloalkyl or fluoro-1-4C-alkyl,
R2 is hydrogen, 1-4C-alkyl or 1-4C-alkoxy-1-4C-alkyl,
R3 is hydrogen, halogen, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32
where
R31 is hydrogen, 1-4C-alkyl, 3-7C-cycloalkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, hydroxypyrrolidino, aziridino, azetidino, piperidino, piperazino, N-1-4C-alkylpiperazino or morpholino group,
X is O (oxygen) or NH and
Ar is a phenyl group, substituted by R4, R5, R6 and R7, wherein
R4 is hydrogen, 1-4C-alkyl, hydroxy-1-4C-alkyl, 1-4C-alkoxy, 2-4C-alkenyloxy, 1-4C-alkylcarbonyl, carboxy, 1-4C-alkoxycarbonyl, carboxy-1-4C-alkyl, 1-4C-alkoxycarbonyl-1-4C-alkyl, halogen, hydroxy, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl,
R5 is hydrogen, 1-4C-alkyl, 1-4C-alkoxy, 1-4C-alkoxycarbonyl, halogen, trifluoromethyl or hydroxy,
R6 is hydrogen, 1-4C-alkyl or halogen and
R7 is hydrogen, 1-4C-alkyl or halogen, and the salts of these compounds.

Among the compounds of formula 1, those of the formula 1 a are preferred

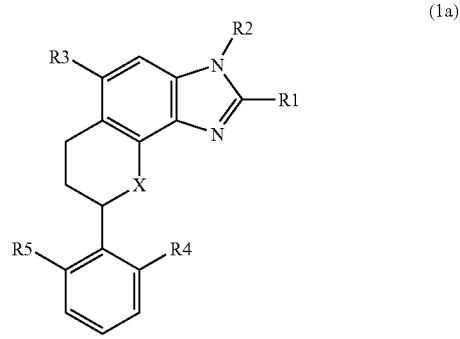

(1a)

in which
R1 is hydrogen, 1-4C-alkyl, 3-7C-cycloalkyl or fluoro-1-4C-alkyl,
R2 is hydrogen, 1-4C-alkyl or 1-4C-alkoxy-1-4C-alkyl,
R3 is hydrogen, halogen, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-1-4C-alkylamino or the group —CO—NR31R32,
where
R31 is hydrogen, 1-4C-alkyl, 3-7C-cycloalkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, hydroxypyrrolidino, aziridino, azetidino, piperidino, piperazino, N-1-4C-alkylpiperazino or morpholino group,
R4 is hydrogen, 1-4C-alkyl, hydroxy-1-4C-alkyl, 1-4C-alkoxy, 1-4C-alkoxycarbonyl, trifluoromethyl, amino, mono- or di-1-4C-alkylamino, 1-4C-alkylcarbonylamino, 1-4C-alkoxycarbonylamino or 1-4C-alkoxy-1-4C-alkoxycarbonylamino,
R5 is hydrogen, 1-4C-alkyl or 1-4C-alkoxy and
X is O (oxygen) or NH,
and the salts of these compounds.

Among the compounds of formula 1, those of the formula 1a are particularly preferred in which
R1 is 1-4C-alkyl, 3-7C-cycloalkyl or fluoro-1-4C-alkyl,
R2 is hydrogen, 1-4C-alkyl or 1-4C-alkoxy-1-4C-alkyl,
R3 is hydrogen, carboxyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, aziridino, azetidino or morpholino group,
R4 is hydrogen,
R5 is hydrogen and
X is O (oxygen) or NH,
and the salts of these compounds.

Exemplified compounds to be mentioned particularly are those of formula 1a, in which
R1 is 1-4C-alkyl, 3-7C-cycloalkyl or fluoro-1-4C-alkyl,
R2 is 1-4C-alkyl or 1-4C-alkoxy-1-4C-alkyl,
R3 is carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, hydroxypyrrolidino, aziridino, azetidino or morpholino group,
R4 is hydrogen,
R5 is hydrogen and
X is O (oxygen) or NH, and the salts of these compounds.

Compounds of embodiment a to be mentioned particularly are those of formula 1, in which
R1 is hydrogen or 1-4C-alkyl,
R2 is hydrogen or 1-4C-alkyl,
R3 is halogen, carboxyl, 1-4C-alkoxycarbonyl, hydroxy-1-4C-alkyl, 1-4C-alkoxy-1-4C-alkyl or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, piperidino, piperazino, N-1-4C-alkylpiperazino or morpholino group,
X is O (oxygen) or NH and
Ar is a phenyl group, substituted by R4, R5, R6 and R7,
wherein
R4 is hydrogen, 1-4C-alkyl, hydroxy-1-4C-alkyl, 1-4C-alkoxy, 2-4C-alkenyloxy, 1-4C-alkylcarbonyl, carboxy, 1-4C-alkoxycarbonyl, carboxy-1-4C-alkyl, 1-4C-alkoxycarbonyl-1-4C-alkyl, halogen, hydroxy, trifluoromethyl, nitro, amino, mono- or di-1-4C-alkylamino, 1-4-C-alkylcarbonylamino, 1-4C-alkoxycarbonylamino, 1-4C-alkoxy-1-4C-alkoxycarbonylamino or sulfonyl,
R5 is hydrogen, 1-4C-alkyl, 1-4C-alkoxy, 1-4C-alkoxycarbonyl, halogen, trifluoromethyl or hydroxy,
R6 is hydrogen, 1-4C-alkyl or halogen and
R7 is hydrogen, 1-4C-alkyl or halogen, and the salts of these compounds.

Among the compounds of formula 1 of embodiment a, those of the formula 1a are preferred, in which
R1 is hydrogen or 1-4C-alkyl,
R2 is hydrogen or 1-4C-alkyl,
R3 is carboxyl, 1-4C-alkoxycarbonyl, hydroxy-1-4C-alkyl, 1-4C-alkoxy-1-4C-alkyl or the group —CO—NR31R32,
where
R31 is hydrogen, 1-7C-alkyl, hydroxy-1-4C-alkyl or 1-4C-alkoxy-1-4C-alkyl and
R32 is hydrogen or 1-7C-alkyl,
or where
R31 and R32 together, including the nitrogen atom to which both are bonded, are a pyrrolidino, piperidino, piperazino, N1-4C-alkylpiperazino or morpholino group,
R4 is hydrogen, 1-4C-alkyl, hydroxy-1-4C-alkyl, 1-4C-alkoxy, 1-4C-alkoxycarbonyl, trifluoromethyl, amino, mono- or di-1-4C-alkylamino, 1-4C-alkylcarbonylamino, 1-4C-alkoxycarbonylamino or 1-4C-alkoxy-1-4C-alkoxycarbonylamino,
R5 is hydrogen, 1-4C-alkyl or 1-4C-alkoxy and
X is O (oxygen) or NH, and the salts of these compounds.

Among the compounds of formula 1 of embodiment a, those of the formula 1a are particularly preferred in which
R1 is 1-4C-alkyl,
R2 is 1-4C-alkyl,
R3 is hydroxy-1-4C-alkyl, 1-4C-alkoxy-1-4C-alkyl or the group —CO—NR31R32,
where
R31 is hydrogen, 1-4C-alkyl, hydroxy-2-4C-alkyl or 1-4C-alkoxy-2-4C-alkyl and
R32 is hydrogen,
or where
R31 and R32 together, including the nitrogen atom to which both are bonded, are a pyrrolidino, group,
R4 is hydrogen,
R5 is hydrogen and
X is O (oxygen) or NH, and the salts of these compounds.

Among the compounds of formula 1 of embodiment a, those exemplified compounds of the formula 1a are particularly preferred in which
R1 is 1-4C-alkyl or fluoro-1-4C-alkyl,
R2 is 1-4C-alkyl or 1-4C-alkoxy-1-4C-alkyl,
R3 is carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl or the group —CO—NR31R32,
where
R31 is hydrogen, 1-4C-alkyl, hydroxy-2-4C-alkyl or 1-4C-alkoxy-2-4C-alkyl and
R32 is hydrogen or 1-4C-alkyl,
or where
R31 and R32 together, including the nitrogen atom to which both are bonded, are a pyrrolidino or morpholino group,
R4 is hydrogen,
R5 is hydrogen and
X is O (oxygen) or NH, and the salts of these compounds.

Preferred subject of the invention are compounds of the formula 2

(2)

in which
R1 is 1-4C-alkyl or 3-7C-cycloalkyl,
R2 is hydrogen or 1-4C-alkyl,

R3 is 1-4C-alkoxycarbonyl, hydroxy-1-4C-alkyl, 1-4C-alkoxy-1-4C-alkyl or the group —CO—NR31R32, where
R31 is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, aziridino, azetidino or morpholino group,
R4 is hydrogen,
R5 is hydrogen and
X is O (oxygen) or NH, and the salts of these compounds.

Preferred exemplified compounds of the invention are those of formula 2, in which
R1 is 1-4C-alkyl, 3-7C-cycloalkyl or fluoro-1-4C-alkyl,
R2 is 1-4C-alkyl or 1-4C-alkoxy-1-4C-alkyl,
R3 is carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, hydroxypyrrolidino, aziridino, azetidino or morpholino group,
R4 is hydrogen,
R5 is hydrogen and
X is O (oxygen) or NH, and the salts of these compounds.

Exemplary preferred compounds are those of the formula 1a, in which R1, R2, R3, R4, R5 and X have the meanings given in the following table 1 (Me=$CH_3$, Et=$C_2H_5$), and the salts of these compounds.

Exemplary particularly preferred compounds are those of the formula 2, in which R1, R2, R3, R4, R5 and X have the meanings given in the following table 1 (Me=$CH_3$, Et=$C_2H_5$), and the salts of these compounds.

TABLE 1

| R1 | R2 | R3 | R4 | R5 | X |
|---|---|---|---|---|---|
| Me | Me | $CH_2OH$ | H | H | O |
| Me | Me | $CH_2OCH_3$ | H | H | O |
| Me | Me | CONHMe | H | H | O |
| Me | Me | CON-pyrrolidine | H | H | O |
| Me | Me | $CONH(CH_2)_2OH$ | H | H | O |
| Me | Me | $CONH(CH_2)_2OMe$ | H | H | O |
| Me | Me | $CONH_2$ | H | H | O |
| Me | Me | CON-morpholine | H | H | O |
| Me | Me | $CONMe_2$ | H | H | O |
| Me | Me | $CH_2O(CH_2)_2OMe$ | H | H | O |
| Me | Me | CON-aziridine | H | H | O |
| Me | Me | COOEt | H | H | O |
| Me | Me | COOH | H | H | O |
| Me | Me | CON-azetidine | H | H | O |
| Me | Me | $CONH(CH_2)_2Me$ | H | H | O |
| Me | Me | $CONHCH_2CHOHCH_2OH$ | H | H | O |
| Me | Me | $NCH_3COCH_3$ | H | H | O |
| Me | Me | $NHCOCH_3$ | H | H | O |
| Me | Me | $NHCOCH_2OMe$ | H | H | O |
| Me | Me | $NHCO(CH_2)_2OMe$ | H | H | O |
| Me | Me | $OCH_2OMe$ | H | H | O |
| Me | Me | $O(CH_2)_2OMe$ | H | H | O |
| Me | Me | CONH-cyclopropyl | H | H | O |

TABLE 1-continued

| R1 | R2 | R3 | R4 | R5 | X |
|---|---|---|---|---|---|
| Me | Me | H | H | H | O |
| Cyclopropyl | Me | $CH_2OCH_3$ | H | H | O |
| Cyclopropyl | Me | CONHMe | H | H | O |
| Cyclopropyl | Me | CON-pyrrolidine | H | H | O |
| Cyclopropyl | Me | $CONH(CH_2)_2OH$ | H | H | O |
| Cyclopropyl | Me | $CONH(CH_2)_2OMe$ | H | H | O |
| Cyclopropyl | Me | $CONH_2$ | H | H | O |
| Cyclopropyl | Me | CON-morpholine | H | H | O |
| Cyclopropyl | Me | $CONMe_2$ | H | H | O |
| Cyclopropyl | Me | $CH_2O(CH_2)_2OMe$ | H | H | O |
| Cyclopropyl | Me | CON-aziridine | H | H | O |
| Cyclopropyl | Me | COOEt | H | H | O |
| Cyclopropyl | Me | COOH | H | H | O |
| Cyclopropyl | Me | CON-azetidine | H | H | O |
| Cyclopropyl | Me | $CONH(CH_2)_2Me$ | H | H | O |
| Cyclopropyl | Me | $CONHCH_2CHOHCH_2OH$ | H | H | O |
| Cyclopropyl | Me | $NCH_3COCH_3$ | H | H | O |
| Cyclopropyl | Me | $NHCOCH_3$ | H | H | O |
| Cyclopropyl | Me | $NHCOCH_2OMe$ | H | H | O |
| Cyclopropyl | Me | $NHCO(CH_2)_2OMe$ | H | H | O |
| Cyclopropyl | Me | $OCH_2OMe$ | H | H | O |
| Cyclopropyl | Me | $O(CH_2)_2OMe$ | H | H | O |
| Cyclopropyl | Me | CONH-cyclopropyl | H | H | O |
| Cyclopropyl | Me | H | H | H | O |
| $CF_3$ | Me | $CH_2OCH_3$ | H | H | O |
| $CF_3$ | Me | CONHMe | H | H | O |
| $CF_3$ | Me | CON-pyrrolidine | H | H | O |
| $CF_3$ | Me | $CONH(CH_2)_2OH$ | H | H | O |
| $CF_3$ | Me | $CONH(CH_2)_2OMe$ | H | H | O |
| $CF_3$ | Me | $CONH_2$ | H | H | O |
| $CF_3$ | Me | CON-morpholine | H | H | O |
| $CF_3$ | Me | $CONMe_2$ | H | H | O |
| $CF_3$ | Me | $CH_2O(CH_2)_2OMe$ | H | H | O |
| $CF_3$ | Me | CON-aziridine | H | H | O |
| $CF_3$ | Me | COOEt | H | H | O |
| $CF_3$ | Me | COOH | H | H | O |
| $CF_3$ | Me | CON-azetidine | H | H | O |
| $CF_3$ | Me | $CONH(CH_2)_2Me$ | H | H | O |
| $CF_3$ | Me | $CONHCH_2CHOHCH_2OH$ | H | H | O |
| $CF_3$ | Me | $NCH_3COCH_3$ | H | H | O |
| $CF_3$ | Me | $NHCOCH_3$ | H | H | O |
| $CF_3$ | Me | $NHCOCH_2OMe$ | H | H | O |
| $CF_3$ | Me | $NHCO(CH_2)_2OMe$ | H | H | O |
| $CF_3$ | Me | $OCH_2OMe$ | H | H | O |
| $CF_3$ | Me | $O(CH_2)_2OMe$ | H | H | O |
| $CF_3$ | Me | CONH-cyclopropyl | H | H | O |
| $CF_3$ | Me | H | H | H | O |
| Me | $CH_2OMe$ | $CH_2OCH_3$ | H | H | O |
| Me | $CH_2OMe$ | CONHMe | H | H | O |
| Me | $CH_2OMe$ | CON-pyrrolidine | H | H | O |
| Me | $CH_2OMe$ | $CONH(CH_2)_2OH$ | H | H | O |
| Me | $CH_2OMe$ | $CONH(CH_2)_2OMe$ | H | H | O |
| Me | $CH_2OMe$ | $CONH_2$ | H | H | O |
| Me | $CH_2OMe$ | CON-morpholine | H | H | O |
| Me | $CH_2OMe$ | $CONMe_2$ | H | H | O |
| Me | $CH_2OMe$ | $CH_2O(CH_2)_2OMe$ | H | H | O |
| Me | $CH_2OMe$ | CON-aziridine | H | H | O |
| Me | $CH_2OMe$ | COOEt | H | H | O |
| Me | $CH_2OMe$ | COOH | H | H | O |
| Me | $CH_2OMe$ | CON-azetidine | H | H | O |
| Me | $CH_2OMe$ | $CONH(CH_2)_2Me$ | H | H | O |
| Me | $CH_2OMe$ | $CONHCH_2CHOHCH_2OH$ | H | H | O |
| Me | $CH_2OMe$ | $NCH_3COCH_3$ | H | H | O |
| Me | $CH_2OMe$ | $NHCOCH_3$ | H | H | O |
| Me | $CH_2OMe$ | $NHCOCH_2OMe$ | H | H | O |
| Me | $CH_2OMe$ | $NHCO(CH_2)_2OMe$ | H | H | O |
| Me | $CH_2OMe$ | $OCH_2OMe$ | H | H | O |
| Me | $CH_2OMe$ | $O(CH_2)_2OMe$ | H | H | O |
| Me | $CH_2OMe$ | CONH-cyclopropyl | H | H | O |
| Me | $CH_2OMe$ | H | H | H | O |
| Me | H | $CH_2OCH_3$ | H | H | O |
| Me | H | CONHMe | H | H | O |
| Me | H | CON-pyrrolidine | H | H | O |
| Me | H | $CONH(CH_2)_2OH$ | H | H | O |
| Me | H | $CONH(CH_2)_2OMe$ | H | H | O |
| Me | H | $CONH_2$ | H | H | O |
| Me | H | CON-morpholine | H | H | O |

TABLE 1-continued

| R1 | R2 | R3 | R4 | R5 | X |
|---|---|---|---|---|---|
| Me | H | CONMe$_2$ | H | H | O |
| Me | H | CH$_2$O(CH$_2$)$_2$OMe | H | H | O |
| Me | H | CON-aziridine | H | H | O |
| Me | H | COOEt | H | H | O |
| Me | H | COOH | H | H | O |
| Me | H | CON-azetidine | H | H | O |
| Me | H | CONH(CH$_2$)$_2$Me | H | H | O |
| Me | H | CONHCH$_2$CHOHCH$_2$OH | H | H | O |
| Me | H | NCH$_3$COCH$_3$ | H | H | O |
| Me | H | NHCOCH$_3$ | H | H | O |
| Me | H | NHCOCH$_2$OMe | H | H | O |
| Me | H | NHCO(CH$_2$)$_2$OMe | H | H | O |
| Me | H | OCH$_2$OMe | H | H | O |
| Me | H | O(CH$_2$)$_2$OMe | H | H | O |
| Me | H | CONH-cyclopropyl | H | H | O |
| Me | H | H | H | H | O |
| Me | Me | H | H | H | NH |
| Cyclopropyl | Me | CH$_2$OCH$_3$ | H | H | NH |
| Cyclopropyl | Me | CONHMe | H | H | NH |
| Cyclopropyl | Me | CON-pyrrolidine | H | H | NH |
| Cyclopropyl | Me | CONH(CH$_2$)$_2$OH | H | H | NH |
| Cyclopropyl | Me | CONH(CH$_2$)$_2$OMe | H | H | NH |
| Cyclopropyl | Me | CONH$_2$ | H | H | NH |
| Cyclopropyl | Me | CON-morpholine | H | H | NH |
| Cyclopropyl | Me | CONMe$_2$ | H | H | NH |
| Cyclopropyl | Me | CH$_2$O(CH$_2$)$_2$OMe | H | H | NH |
| Cyclopropyl | Me | CON-aziridine | H | H | NH |
| Cyclopropyl | Me | COOEt | H | H | NH |
| Cyclopropyl | Me | COOH | H | H | NH |
| Cyclopropyl | Me | CON-azetidine | H | H | NH |
| Cyclopropyl | Me | CONH(CH$_2$)$_2$Me | H | H | NH |
| Cyclopropyl | Me | CONHCH$_2$CHOHCH$_2$OH | H | H | NH |
| Cyclopropyl | Me | NCH$_3$COCH$_3$ | H | H | NH |
| Cyclopropyl | Me | NHCOCH$_3$ | H | H | NH |
| Cyclopropyl | Me | NHCOCH$_2$OMe | H | H | NH |
| Cyclopropyl | Me | NHCO(CH$_2$)$_2$OMe | H | H | NH |
| Cyclopropyl | Me | OCH$_2$OMe | H | H | NH |
| Cyclopropyl | Me | O(CH$_2$)$_2$OMe | H | H | NH |
| Cyclopropyl | Me | CONH-cyclopropyl | H | H | NH |
| Cyclopropyl | Me | H | H | H | NH |
| CF$_3$ | Me | CH$_2$OCH$_3$ | H | H | NH |
| CF$_3$ | Me | CONHMe | H | H | NH |
| CF$_3$ | Me | CON-pyrrolidine | H | H | NH |
| CF$_3$ | Me | CONH(CH$_2$)$_2$OH | H | H | NH |
| CF$_3$ | Me | CONH(CH$_2$)$_2$OMe | H | H | NH |
| CF$_3$ | Me | CONH$_2$ | H | H | NH |
| CF$_3$ | Me | CON-morpholine | H | H | NH |
| CF$_3$ | Me | CONMe$_2$ | H | H | NH |
| CF$_3$ | Me | CH$_2$O(CH$_2$)$_2$OMe | H | H | NH |
| CF$_3$ | Me | CON-aziridine | H | H | NH |
| CF$_3$ | Me | COOEt | H | H | NH |
| CF$_3$ | Me | COOH | H | H | NH |
| CF$_3$ | Me | CON-azetidine | H | H | NH |
| CF$_3$ | Me | CONH(CH$_2$)$_2$Me | H | H | NH |
| CF$_3$ | Me | CONHCH$_2$CHOHCH$_2$OH | H | H | NH |
| CF$_3$ | Me | NCH$_3$COCH$_3$ | H | H | NH |
| CF$_3$ | Me | NHCOCH$_3$ | H | H | NH |
| CF$_3$ | Me | NHCOCH$_2$OMe | H | H | NH |
| CF$_3$ | Me | NHCO(CH$_2$)$_2$OMe | H | H | NH |
| CF$_3$ | Me | OCH$_2$OMe | H | H | NH |
| CF$_3$ | Me | O(CH$_2$)$_2$OMe | H | H | NH |
| CF$_3$ | Me | CONH-cyclopropyl | H | H | NH |
| CF$_3$ | Me | H | H | H | NH |
| Me | CH$_2$OMe | CH$_2$OCH$_3$ | H | H | NH |
| Me | CH$_2$OMe | CONHMe | H | H | NH |
| Me | CH$_2$OMe | CON-pyrrolidine | H | H | NH |
| Me | CH$_2$OMe | CONH(CH$_2$)$_2$OH | H | H | NH |
| Me | CH$_2$OMe | CONH(CH$_2$)$_2$OMe | H | H | NH |
| Me | CH$_2$OMe | CONH$_2$ | H | H | NH |
| Me | CH$_2$OMe | CON-morpholine | H | H | NH |
| Me | CH$_2$OMe | CONMe$_2$ | H | H | NH |
| Me | CH$_2$OMe | CH$_2$O(CH$_2$)$_2$OMe | H | H | NH |
| Me | CH$_2$OMe | CON-aziridine | H | H | NH |
| Me | CH$_2$OMe | COOEt | H | H | NH |
| Me | CH$_2$OMe | COOH | H | H | NH |
| Me | CH$_2$OMe | CON-azetidine | H | H | NH |
| Me | CH$_2$OMe | CONH(CH$_2$)$_2$Me | H | H | NH |
| Me | CH$_2$OMe | CONHCH$_2$CHOHCH$_2$OH | H | H | NH |
| Me | CH$_2$OMe | NCH$_3$COCH$_3$ | H | H | NH |
| Me | CH$_2$OMe | NHCOCH$_3$ | H | H | NH |
| Me | CH$_2$OMe | NHCOCH$_2$OMe | H | H | NH |
| Me | CH$_2$OMe | NHCO(CH$_2$)$_2$OMe | H | H | NH |
| Me | CH$_2$OMe | OCH$_2$OMe | H | H | NH |
| Me | CH$_2$OMe | O(CH$_2$)$_2$OMe | H | H | NH |
| Me | CH$_2$OMe | CONH-cyclopropyl | H | H | NH |
| Me | CH$_2$OMe | H | H | H | NH |
| Me | H | CH$_2$OCH$_3$ | H | H | NH |
| Me | H | CONHMe | H | H | NH |
| Me | H | CON-pyrrolidine | H | H | NH |
| Me | H | CONH(CH$_2$)$_2$OH | H | H | NH |
| Me | H | CONH(CH$_2$)$_2$OMe | H | H | NH |
| Me | H | CONH$_2$ | H | H | NH |
| Me | H | CON-morpholine | H | H | NH |
| Me | H | CONMe$_2$ | H | H | NH |
| Me | H | CH$_2$O(CH$_2$)$_2$OMe | H | H | NH |
| Me | H | CON-aziridine | H | H | NH |
| Me | H | COOEt | H | H | NH |
| Me | H | COOH | H | H | NH |
| Me | H | CON-azetidine | H | H | NH |
| Me | H | CONH(CH$_2$)$_2$Me | H | H | NH |
| Me | H | CONHCH$_2$CHOHCH$_2$OH | H | H | NH |
| Me | H | NCH$_3$COCH$_3$ | H | H | NH |
| Me | H | NHCOCH$_3$ | H | H | NH |
| Me | H | NHCOCH$_2$OMe | H | H | NH |
| Me | H | NHCO(CH$_2$)$_2$OMe | H | H | NH |
| Me | H | OCH$_2$OMe | H | H | NH |
| Me | H | O(CH$_2$)$_2$OMe | H | H | NH |
| Me | H | CONH-cyclopropyl | H | H | NH |
| Me | H | H | H | H | NH |

Particularly preferred are the compounds given as final products of formula 1 in the examples, and the salts of these compounds.

The compounds according to the invention can be synthesised from corresponding starting compounds, for example according to the reaction schemes given below (scheme 1, scheme 2 and scheme 3). The synthesis is carried out in a manner known to the expert, for example as described in more detail in the examples which follow the schemes.

The starting compounds are known, for example, from Gillespie et al., *J. Org. Chem.* 1960, 25 942 (6-chloro-2-methyl-4-nitro-1(3)H-benzimidazole, J. R. E. Hoover, A. R. Day, *J. Amer. Chem. Soc.* 1955, 77, 4324 (4-nitro-1(3)H-benzimidazole-6-carboxamide) or A R. Katritzky et al., *Heterocycles* 1995, 41, 345-452 (4-hydroxy-1-methyl-1H-benzimidazole) or they can be prepared using analogous process steps.

Scheme 1:

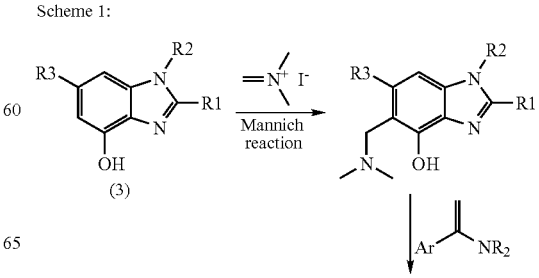

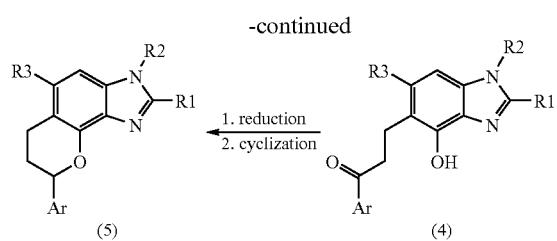

(5)          (4)

Preparation of compounds of the formula 1 where X = O (5), with any desired substituent R1, R2, R3 and Ar Scheme 2:

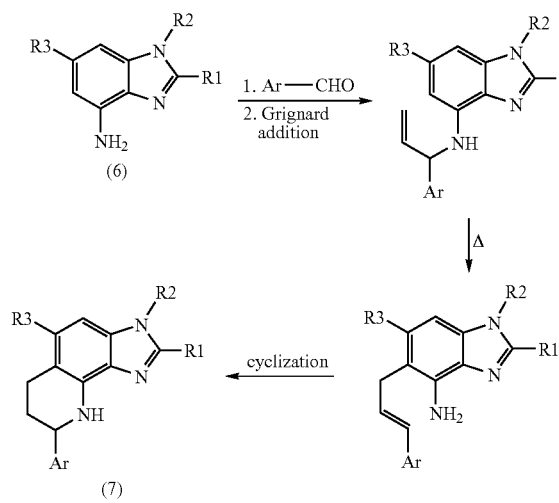

(7)

Preparation of compounds of the formula 1 where X = NH (7), with any desired substituent R1, R2, R3 and Ar The preparation of the compounds of formula 1 where X=O [scheme 1, compounds (5)] can be carried out in a manner known to the person skilled in the art, for example, analogously as described in more detail in International Patent Applications WO 95/27714 and WO 03/014123.

Compounds of the formula 1 where X=NH [scheme 2, compounds (7)] can be obtained according to scheme 2, starting from corresponding substituted 4aminobenzimidazoles known from literature.

The derivatzation, if any, of the compounds obtained according to the above Schemes 1 and 2 (e.g. conversion of a group R3 into another group R3, or of R2=H into another group e. g. R2=1-4C-alkyl) is likewise carried out in a manner known to the expert. If compounds where R3=—CO-1-4C-alkoxy or R3=—CO—NR31R32 are desired, an appropriate derivatization can be performed in a manner known to the expert (e.g. metal catalysed carbonylation of the corresponding halo compound or conversion of an ester into an amide) at the stage of the benzimidazoles of formula 3 or 5 (schemes 1 and 2) or more conveniently at a later point in time.

The compounds of the formula 2 can be isolated from the corresponding racemic mixtures of the formula 1 by techniques known to the expert. The separation can be achieved for example by preparative chromatography using a chiral column, as described in an exemplary manner in the examples.

Alternatively compounds of the formula 2 where X=O, with any desired substituent R1, R2, R3 and Ar can be prepared in a stereoselective way following the reaction steps as outlined generally in scheme 3. Compounds of the formula 8 can be obtained from compounds of the formula 4 by an asymmetric hydrogenation using a chiral hydrogenation catalyst like for example Ruthenium catalysts as described by Noyori et al. in *Angew. Chem.* 2001, 113, 40-75.

Scheme 3:

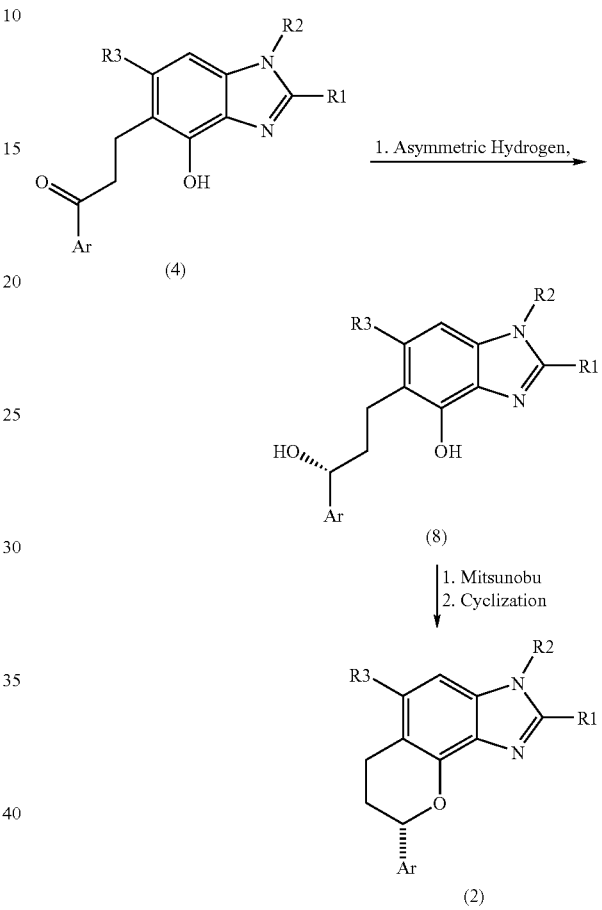

(2)

Preparation of compounds of the formula 2 where X = O, with any desired substituent R1, R2, R3 and Ar Compounds of the formula 4 are known for example from WO 03/014123, or they can be prepared in a known manner, analogously to known compounds.

The following examples serve to illustrate the invention in greater detail without restricting it. Likewise, further compounds of the formula 1 or 2 whose preparation is not described explicitly can be prepared in an analogous manner or in a manner familiar per se to the person skilled in the art using customary process techniques. The abbreviation min stands for minute(s), h for hour(s).

EXAMPLES

Final Products of Formula (1)

1. 2,3-Dimethyl-phenyl-3,6,7,8-tetrahydro-chromeno[7,8-a]imidazole-5-carboxylic Acid Dimethylamide 10 ml Phosphoric acid (85%) were heated to 80° C. for 10 min and then 850 mg (2.3 mmol) 7-hydroxy-6-(3-hydroxy- 3-phenyl-propyl)-2,3-dimethyl-3H-benzimidazole-5-carboxylic acid dimethylamide were added during 10 min. After heating at 80° C. for 1 h, the reaction mixture was poured into ice-water (20 ml) and neutralized with 2M sodium hydroxide solution. The precipitate was filtered off and crystallized from ethyl acetate to give 555 mg (68%) of the title compound as a white solid. m. p. 236°-237° C.

2. 2,3-Dimethyl-8-phenyl-6,7,8,9-tetrahydro-3H-imidazo[4,5-h]quinoline-5-carboxylic Acid Dimethylamide To a solution of 1.5 g (4.2 mmol) 5-bromo-2,3-dimethyl-8-phenyl-6,7,8,9-tetrahydro-3H-imidazo[4,5-h]quinoline in 60 ml dimethylamine (5M solution in tetrahydrofuran) were added 95 mg (0.42 mmol) palladium(II) acetate and 0.66 g (2.5 mmol) triphenylphosphine. The mixture was transferred to an autoclave and carbonylated (6 bar carbon monoxide pressure, 120° C.) for 18 h. The reaction mixture was cooled down, poured into a mixture of saturated ammonium chloride solution (200 ml) and water (100 ml). The mixture was extracted with dichloromethane, the organic layer washed with water, dried over anhydrous magnesium sulphate and evaporated. The residue was purified by column chromatography on silica gel (toluene/dioxane/methanol=6:3.5:0.5). Crystallization from ethyl acetate yielded 0.43 g (29%) of the title compound as a colourless solid. m.p. 167-170° C.

3. 2,3-Dimethyl-8-phenyl-3,6,7,8tetrahydro-chromeno[7,8-d]imidazole-5-carboxylic Acid Amide To a suspension of 0.3 g (0.93 mmol) 2,3-dimethyl-8-phenyl-3,6,7,8-tetrahydro-chromeno[7,8-d]imidazole-5-carboxylic acid in dichloromethane (9 ml) were added 0.45 g (1.4 mmol) O-(1H-benzotriazol-1-yl)-N,N,N', N'-tetramethyluronium tetrafluoroborate (TBTU) and the suspension was stirred for 64 h at room temperature. 11.1 ml (5.6 mmol) Ammonia (0.5 M in dioxane) were added and the mixture was stirred for 24 h at room temperature. The precipitate was filtered off and dried in vacuo at 40° C. to afford 0.15 g (48%) of the title compound as a yellow solid. m.p. 264°-267° C.

4. 2,3-Dimethyl-8-phenyl-4,6,7,8-tetrahydro-chromeno[7,8-d] imidazole-5-carboxylic Acid Methylamide To a suspension of 0.3 g (0.93 mmol) 2,3-dimethyl-8-phenyl-3,6,7,8-tetrahydro-chromeno[7,8-d]imidazole-5-carboxylic acid in dichloromethane (9 ml) were added 0.45 g (1.4 mmol) O-(1H-benzotriazol-1-yl)N,N,N',N'-tetramethyluronium tetrafluoroborate (TBTU) and the suspension was stirred for 64 h at room temperature. 1.2 ml (3.7 mmol) Methylamine (2 M in THF) were added and the mixture was stirred for 24 h at room temperature. The reaction was poured into water and the precipitate filtered off. After drying of the residue in vacuo at 40° C., 35 mg (11%) of the tile compound were isolated as a yellow solid. m.p. 291°-292° C.

5. 2,3 Dimethyl-8-phenyl-3,6,7,8-tetrahydro-chromeno[7,8-d]imidazole-5-carboxylic Acid (2-Hydroxy-ethyl)-amide To a suspension of 0.3 g (0.93 mmol) 2,3-dimethyl-8-phenyl-3,6,7,8-tetrahydro-chromeno[7,8-d]imidazole-5-carboxylic acid in dichloromethane (9 ml) were added 0.45 g (1.4 mmol) O-(1H-benzotriazol-1-yl)-N,N,N',N'-tetramethyluronium tetrafluoroborate (TBTU) and the suspension was stirred for 64 h at room temperature. 284 μl (4.7 mmol) Ethanolamine were added and the mixture was stirred for 24 h at room temperature. The reaction was poured into water and the precipitate filtered off. The residue was purified by chromatography on silica gel (dichloromethane/methanol=15:1) to afford 53 mg (17%) of the title compound as a yellow solid. m.p. 228°-229° C.

6. 2,3-Dimethyl-8-phenyl-3,6,7,8-tetrahydro-chromeno[7,8-d]imidazole-5-carboxylic Acid (2-Methoxy-ethyl)amide To a suspension of 0.3 g (0.93 mmol) 2,3-dimethyl-8-phenyl-3,6,7,8-tetrahydro-chromeno[7,8-d]imidazole-5-carboxylic acid in dichloromethane (9 ml) were added 0.45 g (1.4 mmol) O-(1H-benzotriazol-1-yl)-N,N,N',N'-tetramethyluronium tetrafluoroborate (TBTU) and the suspension was stirred for 64 h at room temperature. 409 μl (4.7 mmol) 2-Methoxy-ethylamine were added and the mixture was stirred for 24 h at room temperature. The reaction was poured into water and the precipitate filtered off. After drying of the residue in vacuo at 40° C., 91 mg (29%) of the title compound were isolated as a yellow solid. m.p. 254°-256° C.

7. 1-(2,3-Dimethyl-8-phenyl-3,6,7,8-tetrahydro-chromeno[7,8-d]imidazol-5-yl)-1-morpholin-4-yl-methanone To a suspension of 0.3 g (0.93 mmol) 2,3-dimethyl-8-phenyl-3,6,7,8-tetrahydro-chromeno[7,8-d]imidazo-5-carboxylic acid in dichloromethane (9 ml) were added 0.45 g (1.4 mmol) O-(1H-benzotriazol-1-yl)-N,N,N',N'-tetramethyluronium tetrafluoroborate (TBTU) and the suspension was stirred for 64 h at room temperature. 410 μl (4.7 mmol) Morpholine were added and the mixture was stirred for 24 h at room temperature. The reaction was poured into water and the precipitate filtered off. After drying of the residue in vacuo at 40° C., 0.1 g (33%) of the title compound were isolated as a yellow solid. m.p. 291°-293° C.

8. 1-(2,3-Dimethylphenyl-3,6,7,8-tetrahydro-chromeno[7,8-d]imidazol-5-yl)-pyrrolidin-1-yl-methanone To a suspension of 0.3 g (0.93 mmol) 2,3-methyl-8-phenyl-3,6,7,8-tetrahydro-chromeno[7,8d]imidazole-5-carboxylic acid in dichloromethane (9 ml) were added 0.45 g (1.4 mmol) O-(1H-benzotriazol-1-yl)-N,N,N',N'-tetramethyluronium tetrafluoroborate (TBTU) and the suspension was stirred for 64 h at room temperature. 392 μl (4.7 mmol) Pyrrolidine were added and the mixture was stirred for 24 h at room temperature. The reaction was poured into water and the precipitate filtered off. After drying of the residue in vacuo at 40° C., 87 mg (28%) of the time compound were isolated as a yellow solid. m.p. 225°-227° C.

9. 2-Isopropyl-3-methyl-8-phenyl-3,6,7,8-tetrahydro-chromeno[7,8-d]imidazole-5-carboxylic Acid Dimethylamide 11.6 ml Phosphoric acid (85%) and 1.2 g (3.0 mmol) 2-isopropyl-7-hydroxy-6-(3-hydroxy-3-phenyl-propyl)-3-methyl-3H-benzoimidazole-5-carboxylic acid dimethylamide were heated at 80° C. for 90 min. After cooling to room temperature the reaction mixture was poured into ice-water, neutralized with 6 N sodium hydroxide solution and extracted with ethyl acetate. The organic layers were dried over magnesium sulphate and concentrated in vacuo. The residue was purified by chromatography on silica gel (dichloromethane/methanol=50:1) to afford 0.4 g (40%) of the title compound as a yellow solid.
m.p. 179°-180° C.

10. 2-Cyclopropyl-3-methyl-8-phenyl-3,6,7,8-tetrahydro-chromeno[7,8-d]imidazole-5-carboxylic Acid Dimethylamide 50 ml Phosphoric acid (85%) and 6.7 g (17.6 mmol) 2-cyclopropyl-7-hydroxy-6-(3-hydroxy-3phenyl-propyl)-3-methyl-3H-benzoimidazol-5-carboxolic acid dimethylamide were heated at 80° C. for 90 min. After cooling to room temperature the reaction mixture was poured into ice-water (400 ml), neutralized with 10N sodium hydroxide solution and extracted with ethyl acetate (4×300 ml). The organic layers were dried over magnesium sulphate and concentrated in vacuo. The residue was purified by chromatography on silica gel (dichloromethane/methanol=100:1) and crystallized from diisopropyl ether to afford 4.5 g (71%) of the title compound as a white solid. m. p. 176°-179° C.

11. 5-Methoxymethyl-2,3-dimethyl-8-phenyl-3,6,7,8-tetrahydro-chromeno[7,8-d]imidazole Oxalic Acid 0.25 g (0.75 mmol) (2,3-Dimethyl-8-phenyl-3,6,7,8-tetrahydro-chromeno[7,8-d]imidazol-5-yl)-methanol were suspended in dichloromethane (10 ml) and 810 µl (1.12 mmol) thionyl chloride were added dropwise. The reaction was stirred at room temperature for 16 h and then concentrated in vacuo. The residue was treated with 1.5 ml (1.5 mmol) sodium methoxide solution (30% in methanol), the mixture transferred in a sealed vessel and heated by microwave irradiation to 100° C. for 15 min. After cooling to room temperature the reaction mixture was poured into water and extracted with dichloromethane. The organic layers were dried over magnesium sulphate and concentrated in vacuo. The residue was, at first, purified by flash chromato-graphy on silica gel (dichloromethane/methanol=80:1) and then treated with oxalic acid in acetone. The precipitate was filtered off and washed with acetone to afford 132 mg (43%) of the title compound as a white solid. m.p. 204°-205° C.

12. 5-(2-Methoxy-ethoxymethyl)-2,3-dimethyl-8-phenyl-3,6,7,8-tetrahydro-chromeno[7,8-d]-imidazole Oxalic Acid 0.23 g (0.75 mmol) (2,3-Dimethyl-8-phenyl-3,6,7,8-tetrahydro-chromeno[7,8-d]imidazol-5yl)-methanol were suspended in dichloromethane (10 ml) and 810 µl (1.12 mmol) thionyl chloride were added dropwise. The reaction was stirred at room temperature for 16 h and then concentrated in vacuo. The residue was treated with 7.5 ml (1.5 mmol) sodium 2-methoxy-ethoxide solution (1M in 2-methoxyethanol) and the mixture stirred at room temperature for 3 h. The solution was poured into water and extracted with dichloromethane. The organic layers were dried over magnesium sulphate and concentrated in vacuo. The residue was, at first, purified by flash chromatography on silica gel (dichloromethane/methanol=20:1) and then treated with oxalic acid in acetone. The precipitate was filtered off and washed with acetone to afford 107 mg (31%) of the title compound as a beige solid. m.p. 131°-133° C.

13. 1-Aziridin-1-yl-(2,3-dimethyl-8-phenyl-3,6,7,8-tetrahydro-chromeno[7,8-d]imidazol-5-yl)-methanone To a suspension of 260 mg (0.81 mmol) 2,3-dimethyl-8-phenyl-3,6,7,8-tetrahydro-chromeno[7,8-d]-imidazole-5-carboxylic acid in tetrahydrofuran (10 ml) were added 157 mg (1.0 mmol) N,N'-carbonyl-diimidazole (CDI) and the reaction was stirred at room temperature overnight 105 mg (2.4 mmol) Aziridine were added and the mixture was stirred for 16 h at room temperature. The reaction was poured into water and extracted with dichloromethane. The organic layers were dried over magnesium sulphate and concentrated in vacuo. The residue was purified by column chromatography on silica gel (dichloromethane/methanol=20:1) and crystallized from n-butanol to afford 56 mg (20%) of the title compound as a white solid. m.p. 201°-204° C.

14. 3-Methyl-8-phenyl-2-trifluoromethyl-3,6,7,8-tetrahydro-chromeno[7,8-d]imidazole-5-carboxylic Acid Dimethylamide 17 ml Phosphoric acid (85%) and 1.7 g (4.0 mmol) hydroxy-(hydroxy-phenyl-propyl)-3-methyl-2-trifluoromethyl-3H-benzoimidazole-5-carboxylic acid dimethylamide were heated at 80° C. for 3 h. After cooling to room temperature the reaction mixture was poured into ice-water, neutralized with 10 N sodium hydroxide solution and extracted with dichloromethane. The organic layers were dried over magnesium sulphate and concentrated in vacuo. The residue was purified by flash chromatography on silica gel (ethyl acetate) and crystallized from diisopropyl ether to afford 210 mg (13%) of the title compound as a white solid. m. p. 223°-225° C.

15. 2,3-Dimethyl-8-phenyl-3,6,7,8-tetrahydro-chromeno[7,8-d]imidazole-5-carboxylic Acid Ethyl Ester 42 ml Phosphoric acid (85%) and 4.2 g (11.4 mmol) 7-hydroxy-6-(3-hydroxy-3-phenyl-propyl)-2,3-di-methyl-3H-benzoimidazole-5-carboxylic acid ethyl ester were heated at 80° C. for 2 h. After cooling to room temperature the reaction mixture was poured into ice-water and neutralized with 10 N sodium hydroxide solution. The precipitate was filtered off and dried in vacuo at 40° C. to afford 3.4 g (86%) of the title compound as a white solid. m. p. 172°-173° C.

16. 2,3-Dimethyl-8-phenyl-3,6,7,8-tetrahydro-chromeno[7,8-d]imidazole-5-carboxylic Acid To a suspension of 3.4 g (9.6 mmol) 2,3-dimethyl-8-phenyl-3,6,7,8-tetrahydro-chromeno[7,8-d]imidazole-5-carboxylic acid ethyl ester in 100 ml dioxane and 25 ml water were added 1.4 g (57.7 mmol) lithium hydroxide and the reaction refluxed for 6 h. After cooling to room temperature, the reaction mixture was adjusted to pH=5 with 2 M HCl solution. The precipitate was filtered off and crystallized with n-butanol to afford 3.0 g (96%) of the title compound as a beige solid of m.p. 323°-326° C.

17. (2,3-Dimethyl-8-phenyl-3,6,7,8-tetrahydro-chromeno[7,8-d]imidazol-5-yl)methanol A solution of 250 mg (0.7 mmol) 2,3-dimethyl-8-phenyl-3,6,7,8-tetrahydro-chromeno[7,8-d]imidazole-5-carboxylic acid ethyl ester in 10 ml tetrahydrofuran was cooled to 0° C. and 927 µl (0.93 mmol) lithium aluminium hydride solution (1 M in THF) were added dropwise. The temperature was raised to room temperature and the reaction stirred for 1 h. To the reaction were cautiously added 1.5 ml water and 1.5 ml 6 M sodium hydroxide solution and the mixture was extracted with dichloromethane. The organic layers were dried over magnesium sulphate and concentrated in vacuo. The residue was purified by column chromatography on silica gel (toluene/dioxane=1:1) and crystallized with diisopropyl ether to afford 101 mg (45%) of the title compound as a beige solid. m.p. 279°-281° C.

18. 1-Azetidin-1-yl-1-(2,3-dimethyl-8-phenyl-3,6,7,8-tetrahydro-chromeno[7,8-d]imidazol-5-yl)-methanone To a suspension of 0.31 g (0.96 mmol) 2,3-dimethyl-8-phenyl-3,6,7,8-tetrahydro-chromeno[7,8-d]imidazole-5-carboxylic acid in dichloromethane (10 ml) were added 0.34 g (1.4 mmol) O-(1H-benzotriazol-1-yl)-N,N,N',N'-tetramethyluronium tetrafluoroborate (TBTU) and the suspension was heated at 40° C. for 4 h. 102 mg (1.0 mmol) Azetidine were added and the mixture was stirred for 3 h. The reaction mixture was poured into water and the extracted with dichloromethane. The organic layers were dried over magnesium sulphate and concentrated in vacuo. The residue was purified by column chromatography on silica gel (toluene/dioxane=1:5) and crystallized with diisopropyl ether to afford 212 mg (61%) of the title compound as a white solid. m.p. 246°-248° C.

19. 2,3Dimethyl-8-phenyl-3,6,7,8-tetrahydro-chromeno[7,8-d]imidazole-5-carboxylic Acid Propyl-amide To a solution of 0.3 g (0.93 mmol) 2,3-dimethyl-8-phenyl-3,6,7,8-tetrahydro-chromeno[7,8-d]imidazole-5-carboxylic acid and 0.3 g (0.93 mmol) O-(1H-benzotriazol-1-yl)-N,N,N',N'-tetramethyluronium tetrafluoroborate (TBTU) in dimethylformamide (5 ml) were added 240 µl (1.9 mmol) triethylamine and 76 µl (0.93 mmol) propylamine and the suspension was stirred overnight at room temperature. The reaction was poured into water, the precipitate filtered off and purified by column chromatography on silica gel (dichloromethane/methanol=50:1) to afford 154 mg (46%) of the toe compound as a white powder.

m.p. 273° C.

20. 1-(2,3-Dimethyl-8-phenyl-3,6,7,8tetrahydro-chromeno[7,8-d]imidazolyl5-yl)-1-3-hydroxy-pyrrolidin-1-yl)methanone To a solution of 0.3 g (0.93 mmol) 2,3-dimethyl-8-phenyl-3,6,7,8-tetrahydro-chromeno[7,8-d]imidazole-5-carboxylic acid and 0.3 g (0.93 mmol) O-(1H-benzotriazol-1-yl)-N,N,N',N'-tetramethyluronium tetrafluoroborate (TBTU) in dimethylformamide (5 ml) were added 240 µl (1.9 mmol) triethylamine and 77 µl (0.93 mmol) 3-pyrrolidinol and the suspension was stirred overnight at room temperature. The reaction was poured into water and the precipitate filtered off. The filtrate was neutralized with saturated sodium bicarbonate solution and extracted with dichloromethane (3×). The organic layers were dried over magnesium sulphate and concentrated in vacuo. The residue was purified by column chromatography on silica gel (dichloromethane/methanol=100:1) to afford 120 mg (33%) of the title compound as a white powder. m.p. 322°-324° C.

21. 2,3-Dimethyl-8-phenyl-3,6,7,8tetrahydro-chromeno[7,8-d]imidazole-5-carboxylic Acid (2,3-Dihydroxy-propyl)amide To a solution of 0.3 g (0.93 mmol) 2,3-dimethyl-8-phenyl-3,6,7,8-tetrahydro-chromeno[7,8-d]imidazole-5-carboxylic acid and 0.3 g (0.93 mmol) O(1H-benzotriazol-1-yl)-N,N,N',N'-tetramethyluronium tetrafluoro-borate (TBTU) in dimethylformamide (5 ml) were added 240 µl (1.9 mmol) triethylamine and 71 µl (0.93 mmol) 3-amino-propane-1,2-diol and the suspension was stirred overnight at room temperature. The reaction was poured into water, the precipitate filtered off and purified by column chromatography on silica gel (dichloromethane/methanol=8:1) to afford 100 mg (270%) of the title compound as a white solid.

m.p. 268°-270° C.

22. 3Methoxymethyl-2-methyl-8-phenyl-3,6,7,8-tetrahydro-chromeno[7,8-d]imidazole-5-carboxylic Acid Dimethylamide A suspension of 0.20 g (0.6 mmol) 7-hydroxy-6-(3-hydroxy-3-phenyl-propyl)-3-methoxymethyl-2-methyl-3H-benzoimidazole-5-carboxylic acid dimethylamide in 2 ml 85% ortho-phosphorlc acid was heated to 80° C. After 90 min stirring, the reaction was cooled to room temperature, poured into ice/water and neutralized with 10M sodium hydroxide. The water layer was extracted with dichloromethane, the organic layers were dried over magnesium sulphate and concentrated in vacuo. The residue was crystallized from ethyl acetate/petroleum ether to afford 130 mg (59%) of the title compound as a beige powder. m.p. 213°-215° C.

23. N-(2,3-Dimethyl-8-phenyl-3,6,7,8-tetrahydro-chromeno[7,8-d]imidazol-5-yl)-N-methyl-acetamide A suspension of 0.75 g (2.0 mmol) N-[7-hydroxy-6-(3-hydroxy-3-phenyl-propyl)-2,3-dimethyl-3H-benzoimidazol-5-yl]-N-methyl-acetamide in 8 ml 85% orthcphosphodc acid was heated to 80° C. After 2 h stirring, the reaction was cooled to room temperature, neutralized with 6M sodium hydroxide and extracted with ethyl acetate (3×20 ml). The organic layers were dried over magnesium sulphate and concentrated in vacuo. The residue was crystallized from ethyl acetate/disopropyl ether (1:10) to afford the title compound (57%) as a beige solid. m.p. 214°-216° C.

24. 2-Ethyl-3-methyl-4-phenyl-3,6,7,8-tetrahydro-chromeno[7,8-d]imidazole-5-carboxylic Acid Dimethylamide A suspension of 1.3 g (3.4 mmol) 2-ethyl-7-hydroxy-6-(3-hydroxy-3-phenyl-propyl)-3-methyl-3H-benzoimidazole-5-carboxylic acid dimethylamide in 13 ml 85% ortho-phosphoric acid was heated to 80° C. After 2 h stirring, the reaction was cooled to room temperature, neutralized with 6M sodium hydroxide (65 ml) and extracted with dichloromethane (4×150 ml). The organic layers were dried over magnesium sulphate and concentrated in vacuo to afford 0.7 g (57%) of the title compound as a white solid. m.p. 195°-197° C.

25. Ethyl 2,3-dimethyl-8-phenyl-6,7,8,9-tetrahydro-3H-imidazo[4,5-h]quinoline-5-carboxylate To a solution of 5.0 g (14 mmol) 5bromo-2,3-dimethyl-8-phenyl-6,7,8,9-tetrahydro-3H-imidazo[4,5-h]-quinoline in 71 ml ethanol and 12 ml triethylamine were added 0.47 g (2.1 mmol) palladium(II) acetate and 1.8 g (6.9 mmol) triphenylphosphine. The mixture was transferred to an autoclave and carbonylated (6 bar carbon monoxide pressure, 100° C.) for 18 h. The reaction mixture was cooled down, poured into water and extracted with dichloromethane. The organic layer was washed with water, dried over anhydrous magnesium sulfate and evaporated. The residue was purified by column chromatography on silica gel (dichloromethane/methanol=13:1). Crystallization from ethyl acetate/light petroleum ether yielded 3.22 g (66%) of the title compound as a colourless solid. m.p. 185-186° C.

26. 2,3-Dimethyl-8-phenyl-6,7,8,9-tetrahydro-3H-imidazo[4,5-h]quinoline-5-carboxylic Acid A suspension of 12 g (3.4 mmol) ethyl 2,3-dimethyl-8-phenyl-6,7,8,9-tetrahydro-3H-imidazo[4,5-h]quinoline-5-carboxylate in 20 ml dioxane and 12 ml 2N aqueous sodium hydroxide was heated to 100° C. until no starting material was left. The mixture was cooled down and neutralized with 2N hydrochloric acid. The precipitate was collected, washed with water and dried. The crude product was recrystallized from ethanol to yield 0.97 g (88%) of the title compound as a colourless solid. m.p. 325-326° C.

27. 2,3-Dimethyl-8-phenyl-6,7,8,9-tetrahydro-3H-imidazo[4,5h]quinoline-5-carboxylic Acid 2-Hydroxyethylamide A suspension of 1.0 g (2.9 mmol) ethyl 2,3-dimethyl-8-phenyl-6,7,8,9-tetrahydro-3H-imidazo[4,5h]-quinoline-5-carboxylate in 10 ml 2-aminoethanol was heated to 140-150° C. until no starting material was left. The mixture was partitioned between saturated aqueous ammonium chloride and dichloro-methane/methanol 9:1. The organic layer was separated, dried over anhydrous magnesium sulphate and evaporated. The residue was purified by column chromatography on silica gel (toluene/dioxane/methanol=6:3:1). Crystallization from diisopropyl ether yielded 0.55 g (52%) of the title compound as a colourless solid. m.p. 248-251° C.

28. 2,3-Dimethyl-8-phenyl-6,7,8,9-tetrahydro-3H-imidazo[4,5h]quinoline-5-carboxylic Acid Amide To a suspension of 0.9 g (2.8 mmol) 2,3-dimethyl-8-phenyl-6,7,8,9-tetrahydro-3H-imidazo[4,5h]quinoline-5-carboxylic acid in 10 ml tetrahydrofuran and 8 ml N,N-dimethylformamide were added 0.5 g (3.1 mmol) N,N'-carbonyldiimidazole. After 4 h at 60° C., the solution was cooled down and ammonia was bubbled through the flask for 4 h. The mixture was allowed to stand 60 h and then poured into 100 ml water. The precipitate was collected, washed with water and dried at 50° C. to yield 0.64 g (71%) of the title compound. m.p. 311-319° C.

29. 2,3-Dimethyl-8-phenyl-6,7,8,9-tetrahydro-3H-imidazo[4,5-h]quinoline-5-carboxylic Acid Methylamide To a suspension of 1.0 g (3.1 mmol) 2,3-dimethyl-8-phenyl-6,7,8,9-tetrahydro-3H-imidazo[4,5-h]quinoline-5-carboxylic acid in 10 ml tetrahydrofuran and 5 ml N,N-dimethylformamide were added 1.0 g (6.2 mmol) N,N'-carbonyldiimidazole. After 1 h at 60° C., the solution was cooled down and 15.6 ml (31.2 mmol) methylamine (2M in tetrahydrofuran) were added. The mixture was stirred 2 h at ambient temperature and then poured into 50 ml water. The precipitate was collected, washed with water and dried at 50° C. to yield 0.87 g (84%) of the title compound. m.p. 259° C.

30. 2,3-Dimethyl-8-phenyl-6,7,8,9-tetrahydro-3H-imidazo[4,5-h]quinoline-5-carboxylic Acid 1-aziridinylamide To a suspension of 0.47 g (1.5 mmol) 2,3-dimethyl-8-phenyl-6,7,8,9-tetrahydro-3H-imidazo[4,5h]quinoline-5-carboxylic acid in 10 ml tetrahydrofuran and 5 ml N,N-dimethylformamide were added 0.4 g (2.5 mmol) N,N'-carbonyldiimidazole. After 1 h at 60° C., the solution was cooled down and 0.8 g (18.6 mmol) aziridine were added in 4 portions over a period of 3 h. After complete reaction, the organic layer was separated, dried over anhydrous magnesium sulfate and evaporated. The residue was purified by column chromatography on silica gel (ethyl acetate/light petroleum ether=7:3). Crystallization from diethyl ether/n-heptane yielded 0.23 g (46%) of the title compound as a colourless solid. m.p. 192-193° C.

31. 5-Hydroxymethyl-2,3-dimethyl-8-phenyl-6,7,8, 9tetrahydro-3H-imidazo[4,5-h]quinoline To a suspension of 0.2 g (5.3 mmol) lithium aluminium hydride in 15 ml tetrahydrofuran was slowly added a solution of 1.0 g (2.9 mmol) ethyl 2,3-dimethyl-8-phenyl-6,7,8, 9-tetrahydro-3H-imidazo[4,5-h]quinoline-5-carboxylate in 5 ml tetrahydrofuran. After 2 h, the reaction mixture was carefully hydrolyzed with 0.1 ml water, 0.2 ml 6N aqueous potassium hydroxide and 0.1 ml water. Anhydrous magnesium sulfate was added and the mixture was stirred 1 h. After filtration through celite, the filtrate was evaporated and the residue purified by column chromatography on silica gel (dichloromethane/methanol=13:1). Crystallization from acetone yielded 0.28 g (32%) of the title compound as a colourness solid. m.p. 253-254° C.

32. (8S)- and (8R)-2,3-Dimethyl-8-phenyl-6,7,8,9-tetrahydro-3H-imidazo[4,5h]quinoline-5-carboxylic Acid Methylamide Resolution of racemic 2,3-dimethyl-8-phenyl-6,7,8,9-tetrahydro-3H-imidazo[4,5h]quinoline-5carboxylic Acid Methylamide was achieved by preparative chromatography using a 250×110 mm CHIRALCEL® OD 20 μm column. The mobile phase consisted of 100% acetonftrile. The separation was performed at room temperature with a flow rate of 500 ml/min. The products were detected at a wavelength of 310 nm. The separation afforded 0.78 g (8S)-2,3-dimethyl-8-phenyl-6,7,8,9-tetrahydro-3H-imidazo[4,5-h] quinoline-5-carboxylic acid methylamide (ee>99.9%, m.p. 273-275° C.) and 0.79 g (8R)-2,3-dimethyl-8-phenyl-6,7,8, 9-tetrahydro-3H-imidazo[4,5-h]quinoline-5-carboxylic acid methylamide (ee 98.9%, m.p. 272-273° C.), both as colourless solids. The optical purity was examined by means of optical rotation. For the (8S)-enantiomer $[a]^D{}_{20}$=−42 (c=0.1, dichloromethane) was determined.

33. (8S)-2,3-Dimethyl-8-phenyl-3,6,7,8-tetrahydro-chromeno[7,8-d]imidazole-5-carboxylic Acid Dimethylamide Resolution of racemic 2,3-dimethyl-8-phenyl-3,6,7,8-tetrahydro-chromeno[7,8-d]imidazole-5-carboxylic acid dimethylamide (0.5 g, 1.4 mmol) was achieved by preparative chromatography using a 275×110 mm CHIRALPAK® AS-V 20 µm column. The mobile phase consisted of a n-heptan/ethanol/diethylamine mixture [95/5/0.1 (v/v/v)]. The separation was performed at room temperature with a flow rate of 1 ml/min. The products were detected at a wavelength of 225 nm. The separation afforded 0.19 g (39%; ee 98.9%) of the title compound ((8S)-enantiomer) as a white solid. m.p. 227°-228° C.

The optical purity was examined by means of optical rotation. For the title compound ((8S)-enantiomer) an $[a]^D_m$ value of −89° (c=0.1, dichloromethane) was determined.

34. (8R)-2,3-Dimethyl-8-phenyl-3,6,7,8-tetrahydro-chromeno[7,8-d]imidazole-5-carboxylic Acid Dimethylamide Resolution of racemic 2,3-dimethylphenyl-3,6,7,8-tetrahydro-chromeno[7,8-d]imidazole-5-carboxylic acid dimethylamide (0.5 g, 1.4 mmol) was achieved by preparative chromatography using a 275×110 mm CHIRALPAK® AS-V 20 µm column. The mobile phase consisted of a n-heptan/ethanol/diethylamine mixture [95/5/0.1 (v/v/v)]. The separation was performed at room temperature with a flow rate of 1 ml/min. The products were detected at a wavelength of 225 nm. The separation afforded 0.19 g (39%; ee 99.8%) of the title compound ((8R)-enantiomer) as a white solid. m.p. 227°-228° C.

The optical purity was examined by means of optical rotation. For the title compound ((8R)-enantiomer) an $[a]^D_{20}$ value of +94° (c=0.1, dichloromethane) was determined.

35. 2,3-Dimethyl-8-phenyl-3,6,7,8-tetrahydro-chromeno[7,8-d]imidazole-5-carboxylic Acid Cyclopropylamide To a suspension of 0.5 g (1.5 mmol) 2,3-dimethyl-8-phenyl-3,6,7,8-tetrahydro-chromeno[7,8-d]imidazole-5-carboxylic acid in dichloromethane (15 ml) were added 0.75 g (2.3 mmol) O-(1H-benzotriazol-1-yl)-N,N,N',N'-tetramethyluronium tetrafluoroborate (TBTU) and the suspension was stirred overnight at room temperature. 430 µl (6.2 mmol) Cyclopropylamine were added and the mixture was stirred at room temperature for 1 h. The reaction mixture was poured into water (30 ml) and extracted with dichloromethane (3×20 ml). The organic layers were dried over magnesium sulphate and concentrated in vacuo. The residue was crystallized from ethanol to afford 345 mg (62%) of the title compound as a white solid.

m.p. 312°-313° C.

36. 2,3-Dimethyl-8-phenyl-3,6,7,8-tetrahydro-chromeno[7,8-d]imidazole

A suspension of 5 ml phosphoric acid (85%) and 260 mg (0.9 mmol) 1,2-dimethyl-5-(3phenyl-allyl)-1H-benzimidazol-4-ol was heated at 90° C. for 90 min. After cooling to room temperature, the reaction mixture was poured into water (400 ml), neutralized with 6N sodium hydroxide solution and extracted with dichloromethane (4×300 ml). The organic layers were dried over magnesium sulphate and concentrated in vacuo. The residue was purified by column chromatography on silica gel (toluene/dioxane=2:1) to afford 24.5 mg (10%) of the title compound as a white solid. m. p. 161°-164° C.

37. 2-Methyl-8-phenyl-3,6,7,8-tetrahydro-chromeno[7,8-d]imidazole-5-carboxylic Acid Dimethylamide A suspension of 0.69 g (1.4 mmol) 7-hydroxy-6-(2-hydroxy-3-phenyl-propyl)-2-methyl-3-(2-trimethylsilanyl-ethoxymethyl)-3H-benzimidazole-5-carboxylic acid dimethylamide and 7 ml phosphoric acid (85%) was heated at 80° C. for 1 h. After cooling to room temperature, the reaction mixture was poured into water and neutralized with 6N sodium hydroxide solution. The precipitate was filtered off and purified by column chromatography on silica gel (dichloromethane/methanol=10:1) to afford 0.34 g (72%) of the title compound as a yellow foam.

38. (S)-2,3-Dimethyl-8-phenyl-3,6,7,8-tetrahydro-chromeno[7,8-d]imidazole-5-carboxylic Acid Dimethylamide (314853)

A solution of 0.4 g (1.1 mmol) 7-hydroxy-((R)-3-hydroxy-3-phenyl-propyl)-2,3-dimethyl-3H-benzimidazole-5-carboxylic acid dimethylamide in 20 ml dry tetrahydrofurane was treated with 0.66 g (3.3 mmol) DIAD and 0.82 g (3.2 mmol) triphenylphosphine and the reaction mixture was stirred at room temperature for 1 h. The reaction was poured into a satured ammonium chloride solution (10 ml) and extracted with ethyl acetate. The organic layers were dried over magnesium sulphate and concentrated in vacuo. The residue was purified by column chromatography on silica gel (ethyl acetate/methanol=20:1) to afford 0.15 g (42%) of the title compound as a white solid. m.p. 229°-231° C. $[\alpha]_D$=−47° (c=0.2 ln CHCl$_3$). The optical purity was determined by chiral HPLC: column: CHIRALPAK® AD-H 250×4.6 mm, 5 µm; solvent: ethanol/ethanol=1:1 (v/v)+ 0.1% diethylamine, flow rate: 1 ml/min.

The (8S)-enantiomer (99.31 area,) and the (8R)-enantiomer (0.55 area %) were eluted at retention times of 3.91 min and 4.06 min, respectively.

Starting Compounds and Intermediates

A. 2-Benzyloxy-4-bromo-6-nitro-phenylamine

To a suspension of 50 g (325 mmol) 2-amino-nitrophenol, 45 g (325 mmol) potassium carbonate and 2 g (13 mmol) sodium iodide in 400 ml ethanol were added 47 ml (408 mmol) benzyl chloride and the mixture was heated to 80° C. After 2 h, the reaction mixture was cooled down and the solvent was evaporated. The residue was dissolved in ethyl acetate and extracted with water. The organic layer was dried over anhydrous magnesium sulphate and evaporated. Coevaporation with dichloromethane (three times) led to a dark brown oily residue which was dissolved in 400 ml acetonitrile. After addition of 63.4 g (356 mmol) N-bromosuccinimide, the reaction mixture was refluxed for 1 h. After cooling down, 400 g silica gel were added and the mixture was evaporated to dryness. The resulting solid was put on a column and the product was eluted with ethyl acetate/light petroleum ether (4:1). Evaporation of the eluent afforded a solid which was recrystallized from ethyl acetate/heptane to give 62 g (59%) of the title compound as a red solid. m.p. 90° C.

B. N-Acetyl-N-(2-benzyloxy-4-bromo-nitro-phenyl) acetamide

A suspension of 20 g (62 mmol) 2-benzyloxy-4-bromo-6-nitrophenylamine in 120 ml acetic anhydride and 2 ml methanesulphonic add was heated to 120° C. After complete reaction (15 min), excess acetic anhydride was evaporated in vacuo. The residue was dissolved in dichloromethane/water and neutralized with 6N aqueous sodium hydroxide. The organic layer was separated, dried over anhydrous magnesium sulphate and evaporated. Crystallization of the residue from ethyl acetate/n-heptane yielded 23.2 g (92%) of the title compound as a cream-coloured solid. m.p. 148° C.

C. N-(2-Amino-6-benzyloxy-4-bromo-phenyl)acetamide

A suspension of 23 g (56 mmol) N-acetyl-N-(2-benzyloxy4-bromo-6-nitro-phenyl)-acetamide, 5.5 g (34 mmol) iron(III) chloride and 13.8 g activated charcoal in 600 ml methanol was heated to reflux. To the reaction mixture were added 28 ml hydrazine hydrate (95%) to maintain gentie reflux. After complete reaction (2 h), the reaction mixture was cooled down and filtered through celite. The filter cake was washed thoroughly with dichloromethane/methanol and the filtrate was evaporated to dryness. The residue was partitioned between dichloromethane/methanol and water. The organic layer was washed with brine, dried over anhydrous magnesium sulphate and evaporated. The residue was recrystallized from boiling ethyl acetate/n-heptane to give 12.3 g (65%) of the title compound as a colourless solid. m.p. 185° C.

D. N-(2-Benzyloxy-4-bromo-6-dimethylamino-phenyl)acetamide

A suspension of 5 g (15 mmol) N-(2-amino-6-benzyloxy-4-bromo-phenyl)-acetamide in 80 ml methanol and 34 ml formaldehyde (37%) was acidified with saturated methanolic hydrogen chloride to give a clear yellow solution. To the solution were added 1.5 g (24 mmol) sodium cyanoborohydride in small portions. After complete reaction (15 min), the mixture was neutralized with aqueous sodium hydrogen carbonate and extracted with dichloromethane. The organic layer was dried over anhydrous magnesium sulphate and evaporated. Crystallization of the residue from ethyl acetate/ heptane yielded 4.3 g (79%) of the title compound as a colourless solid. m.p. 177° C.

E-4-Benzyloxy-6bromo-1,2-dimethyl-1H-benzimidazole

A suspension of 26.2 g (72 mmol) N-(2-benzyloxy-4-bromo-6-dimethylamino-phenyl)-acetamide in 180 ml phosphoryl chloride was heated to 70° C. for 24 h. The excess of phosphoryl chloride was evaporated in vacuo. The residue was suspended in dichloromethane and carefully neutralized with 6N aqueous potassium hydroxide and water. The organic layer was separated, dried over anhydrous magnesium sulphate and evaporated. Crystallization of the residue from ethyl acetate yielded 15.1 g (63%) of the title compound as a colourless solid. m.p. 177-179° C.

F. 7-Benzyloxy-2,3-dimethyl-3H-benzimidazole-5-carboxylic Acid Dimethylamide To a solution of 3 g (9.1 mmol) 4-benzyloxy-6-bromo-1,2-dimethyl-1H-benzimidazole in 100 ml dimethylamine (3.2M solution in tetrahydrofuran) were added 0.3 g (1.3 mmol) palladium(II) acetate and 1.4 g (5.3 mmol) triphenylphosphine. The mixture was transferred to an autoclave and carbonylated (6 bar carbon monoxide pressure, 120° C.) for 16 h. The reaction mixture was cooled down, evaporated and the residue was dissolved in dichloromethane. The organic layer was extracted with water, dried over anhydrous magnesium sulphate and evaporated. Purification of the residue by column chromatography on silica gel using ethyl acetate yielded 2.3 g (78%) of the title compound as a colourless solid m.p. 159-160° C.

G. 7-Hydroxy-2,3-dimethyl-3H-benzoimidazole-carboxylic Acid Dimethylamide

A solution of 2.3 g (7.1 mmol) 7-Benzyloxy-2,3-dimethyl-3H-benzimidazole-5-carboxylic acid dimethyl-amide in 80 ml methanol was hydrogenated over 0.3 g 10% Pd/C (1 bar H for 16 h. The catalyst was filtered off and the filtrate was evaporated. The residue was crystallized from acetone to give 1.2 g (71%) of the title compound as a colourless solid. m.p. 248° C.

H. 6-Dimethylaminomethyl-7-hydroxy-2,3-dimethyl-3H-benzimidazole-5-carboxylic Acid Dimethylamide To a suspension of 2.0 g (8.6 mmol) 7-Hydroxy-2,3-dimethyl-3H-benzimidazole-5-carboxylic acid dimethylamide in dichloromethane (80 ml) was added dropwise a suspension of 1.7 g (9.4 mmol) Eschenmoser's salt in dichloromethane (50 ml). After stirring for 3 h at room temperature, the reaction mixture was poured into saturated sodium bicarbonate solution (100 ml) and extracted with dichloromethane (2×50 ml). The organic layers were dried over magnesium sulphate and concentrated in vacuo to give 20 g (82%) of the title compound as an orange foam. The compound was used for the next step without further purification.

$^1$H-NMR (200 MHz; DMSO): δ=2.31 (s, 3H, Me), 2.58 (2s, 6H, 2 NC$H_3$), 2.78 (s, 3H, NC$H_3$), 3.02 (s, 3H, NC$H_3$), 3.62 (m, 5H, C$H_3$N, NC$H_3$), 7.79 (s, 1 H, Ar$H$).

I. 7-Hydroxy-2,3-dimethyl-6-(3-oxo-3-phenyl-propyl)-3H-benzimidazole-5-carboxylic Acid Dimethylamide 2.0 g (6.9 mmol) 6-dimethylaminomethyl-7-hydroxy-2,3-dimethyl-3H-benzimidazole-5-carboxylic acid dimethylamide and 1.8 g (10.3 mmol) 1-(1-phenyl-vinyl)-pyrrolidine were suspended in toluene (40 ml) and the reaction was refluxed over night. After cooling to room temperature, the solvent was concentrated in vacuo. The residue was purified by column chromatography on silica gel (dichloromethane/ methanol, 14:1). Crystallization from ethyl acetate afforded 1.1 g (42%) of the title compound as a beige solid. m. p. 223°-224° C.

J. 7-Hydroxy-6-(3-hydroxy-3-phenyl-propyl)-2,3-dimethyl-3H-benzimidazole-5-carboxylic Acid Dimethylamide To a suspension of 1.0 g (2.7 mmol) 7-hydroxy-2,3-dimethyl-6-(3-oxo-3-phenyl-propyl)-3H-benzo-imidazole-5-carboxylic acid dimethylamide in ethanol (10 ml) were cautiously added 124 mg (3.3 mmol) sodium borohydride (exothermic reaction 1) and the reaction was stirred for 2 h at room temperature. The reaction mixture was poured into saturated ammonium chloride solution (20 ml) and diluted with water (80 ml). The precipitate was filtered off and dried in vacuo to afford 880 mg (89%) of the title compound as a beige solid. m. p. 257°-260° C.

K. 6-Bromo-2-methyl-4-nitro-1(3)H-benzimidazole

To a suspension of 65 g (0.28 mol) 4bromo-6-nitro-1,2-phenylenediamine in 600 ml ethanol were added 140 ml 5N hydrochloric acid. The reaction mixture was refluxed and 58 ml (0.56 mol) of 2,4-pentanedione were added in one portion. After 1 h, the mixture was cooled down, poured into 500 ml water and neutralized with conc. ammonia. The precipitate was collected, washed thoroughly with water and dried over phosphorus pentoxide to give 70.8 g (99%) of the title compound as a white solid.

M.p. 229-231° C.

L. 6-Bromo-1,2-dimethyl-4-nitro-1H-benzimidazole

To a suspension of 4.3 g (107 mmol) sodium hydride (60% w/w dispersion in mineral oil) in 25 ml N,N-dimethylformamide was slowly added a solution of 25 g (98 mmol) 6bromo-2-methyl-nitro-1(3)H-benzimidazole in 100 ml N,N-dimethylformamide at 0° C. After 30 min at 0° C., 15.2 g (107 mmol) methyliodide were added over 20 min. When the reaction was finished (45 min), 200 ml water were carefully added and the mixture was stirred for 1 h at room temperature. The precipitate was collected, washed thoroughly with water and dried over phosphorus pentoxide in vacuo. Recrystallization from methanol yielded 19.6 g (74%) of the title compound as a colourless solid. m.p. 193-195° C.

M. 6-Bromo-1,2-dimethyl-1H-benzimidazol-4-ylamine

To a solution of 19 g (70 mmol) 6-bromo-1,2-dimethyl-4-nitro-1H-benzimidazole in 250 ml methanol were added 13.7 g (84 mmol) iron(III) chloride and 6 g activated charcoal. The reaction mixture was heated to 80° C. and 17 ml hydrazine hydrate (95%) were slowly added. After refluxing for 3 h, the hot reaction mixture was filtered through celite and the precipitate was washed with methanol and dichloromethane. The filtrate was evaporated to give a suspension, which was treated with n-heptane. The precipitate was collected, washed with n-heptane and dried in vacuo to give 13.3 g (79%) of the title compound as a white solid. m.p. 206-209° C.

N. (6-Bromo-1,2-dimethyl-1H-benzimidazol-4-yl)-(1-phenyl-allyl)-amine 6.4 g (26.7 mmol) 6-bromo-1,2-dimethyl-1H-benzimidazol-4-ylamine, 8.5 g (80 mmol) benzaldehyde and 0.3 g p-toluenesulphonic acid monohydrate in 80 ml toluene were refluxed on a Dean-Stark-trap. After complete reaction, the mixture was evaporated to one third of its volume and diluted with 50 ml tetrahydrofuran. The mixture was cooled to 0° C. and 80 ml (80 mmol) vinylmagnesiumbromide (1M solution in tetrahydrofuran) were added during 45 min. After 30 min., the reaction mixture was hydrolyzed with saturated ammonium chloride solution, diluted with water and extracted with ethyl acetate. The organic phase was separated, washed with water, dried over anhydrous magnesium sulphate and evaporated. The residue was purified by column chromatography on silica gel (petroleum ether/ethyl acetate=7:3). Crystallization from diisopropyl ether afforded 4.2 g (44%) of the title compound as a colourless solid. m.p. 137-139° C.

O. 6-Bromo-1,2-dimethyl-5-(3-phenyl-allyl)-1H-benzimidazol-4-ylamine

A suspension of 3.8 g (10.7 mmol) (6-bromo-1,2-dimethyl-1H-benzimidazol-4-yl)-(1-phenyl-allyl)-amine and 3.5 g p-toluenesulphonic acid monohydrate in 80 ml toluene was refluxed for 26 h. The suspension was poured into a mixture of 50 ml saturated sodium hydrogencarbonate solution and 150 ml water and extracted with ethyl acetate. The organic phase was separated, dried over anhydrous magnesium sulfphate and evaporated. The residue was purified by column chromatography on silica gel (toluene/dioxane/methanol=6:3.8:0.2). Crystallization from diisopropyl ether gave 2.45 g (64%) of the title compound as a colourless solid. m.p. 186-189° C.

P. 5-Bromo-2,3-dimethyl-8-phenyl-6,7,8,9-tetrahydro-3H-imidazo[4,5-h]quinoline A suspension of 2.0 g (5.6 mmol) 6-bromo-1,2-dimethyl-5-(3-phenyl-allyl)-1H-benzimidazol-4-ylamine in 10 ml phosphoric acid (85%) was heated to 130° C. for 20 min. The solution was poured onto crushed ice and the pH adjusted to pH=9 by the addition of 6N sodium hydroxide solution. The mixture was extracted with dichloromethane/methanol (10:1), the organic phase was separated, dried over anhydrous magnesium sulphate and evaporated. The residue was purified by column chromatography on silica gel (toluene/dioxane/methanol=6:3.8:02). Crystallization from diisopropyl ether yielded 1.7 g (84%) of the title compound as a colourless solid. m.p. 206-210° C.

Q. 2,3-Dimethyl-8-phenyl-3,6,7,8-tetrahydro-chromeno[7,8-d]imidazole-5-carboxylic Acid To a suspension of 3.3 g (9.6 mmol) 2,3dimethyl-8-phenyl-3,6,7,8-tetrahydro-chromeno[7,8d]imidazole-5-carboxylic acid ethyl ester in dioxane (100 ml) were added 1.4 g (57.7 mmol) lithium hydroxide in 25 ml water and the mixture was refluxed for 5 h. After cooling to room temperature, the reaction was poured into water and the pH adjusted to pH=5 with 2 N HCl. The precipitate was filtered off and crystallized from n-butanol to afford 3.0 g (96%) of the title compound as a beige solid. m.p. 323°-326° C.

R. 7-Hydroxy-6-(3-hydroxy-3-phenyl-propyl)-2-isopropyl-3-methyl-3H-benzimidazole-5-carboxylic Acid Dimethylamide A solution of 1.3 g (3.3 mmol) 7-hydroxy-2-isopropyl-3-methyl-6-3-oxo-3-phenyl-propyl)-3H-benzimidazole-5-carboxylic acid dimethylamide in ethanol (10 ml) was treated with 201 mg (5.3 mmol) sodium borohydride and the reaction was stirred at room temperature for 2.5 h. A saturated ammonium chloride solution was added and the reaction stirred for further 30 min. The reaction mixture was poured into water (60 ml) and extracted with dichloromethane. The organic layers were dried over magnesium sulphate and concentrated in vacuo to afford 1.2 g (92%) of the title compound as a green wax.

S. 7-Hydroxy-6-(3-hydroxy-3-phenyl-propyl)-2,3-dimethyl-3H-benzimidazole-5-carboxylic Acid Ethyl Ester A solution of 4.6 g (12.5 mmol) 7-hydroxy-2,3-dimethyl-6-(3-oxo-phenylpropyl)-3H-benzimidazole-5-carboxylic acid ethyl ester in ethanol (200 ml) was treated with 570 mg (15.0 mmol) sodium borohydride and the reaction was stirred at room temperature for 3 h. A saturated ammonium chloride solution was added and the reaction was poured into water (200 ml). The precipitate was filtered off and dried in vacuo at 40° C. to afford 4.4 g (95%) of the title compound as a white solid. m.p. 193°-195° C.

T. 7-Hydroxy-6-(3-hydroxy-3-phenyl-propyl)-3-methyl-2-trifluoromethyl-3H-benzimidazole-5-carboxylic Acid Dimethylamide A solution of 3.0 g (7.2 mmol) 7-hydroxy-3-methyl-6-(3-oxo-3-phenyl-propyl)-2-trifluoromethyl-3H-benzimidazole-5-carboxylic acid dimethylamide in ethanol (100 ml) was treated with 324 mg (8.6 mmol) sodium borohydride and the reaction was stirred at room temperature for 3 h. A saturated ammonium chloride solution was added, the reaction was poured into water (100 ml) and extracted with dichloromethane. The organic layers were dried over magnesium sulphate and concentrated in vacuo to afford 3.0 g (98%) of the title compound as a brown foam.

U. 2-Cyclopropyl-7-hydroxy-6-(3-hydroxy-3-phenyl-propyl)-3-methyl-3H-benzimidazole-5-carboxylic Acid Dimethylamide A solution of 1.5 g (4.0 mmol) 2-cyclopropyl-7-hydroxy-3-methyl-6-(3-oxo-3-phenyl-propyl)-3H-benzoimidazole-5-carboxylic acid dimethylamide in ethanol (22 ml) was treated with 283 mg (6.3 mmol) sodium borohydride and the reaction was stirred at room temperature for 3 h. A saturated ammonium chloride solution was added, the reaction was poured into water and extracted with dichloromethane (3×100 ml). The organic layers were dried over magnesium sulphate and concentrated in vacuo to afford 1.5 g (100%) of the title compound as a orange-brown solid. m.p. 92+-94° C.

V. 7-Hydroxy-2,3-dimethyl-6-(3-oxo-3-phenyl-propyl)-3H-benzimidazole-5-carboxylic Acid Ethyl Ester A suspension of 12.5 g (53.4 mmol) 7-hydroxy-2,3-dimethyl-3H-benzimidazole-5-carboxylic acid ethyl ester in dry dichloromethane (500 ml) was treated with 12.8 g (69.4 mmol) N,N-dimethylmethylenimmonium iodide and the reaction was stirred at room temperature for 8 h. The mixture was concentrated in vacuo and the residue (13.8 g) was suspended in toluene (500 ml). 12.1 g (70 mmol) acetophenone pyrrolidine enamine were added and the suspension was heated at 100° C. for 6 h. After cooling to room temperature, the solvent was removed in vacuo, the residue was dissolved in dichloromethane and treated with a solution of fumaric acid in methanol. The precipitate was filtered off, dissolved in water and the pH was adjusted to pH=7 with saturated sodium bicarbonate solution. The precipitate was filtered off and dried in vacuo at 40° C. to afford 8.3 g (48%) of the title compound as a white solid. m.p. 205°-206° C.

W. 2-Cyclopropyl-7-hydroxy-3-methyl-6-(3-oxo-3-phenyl-propyl)-3H-benzimidazole-5-carboxylic Acid Dimethylamide A suspension of 8.5 g (32.8 mmol) 2-cyclopropyl-7-hydroxy-3-methyl-3H-benzimidazole-5-carboxylic acid dimethylamide in dry dichloromethane (500 ml) was treated with 6.6 g (36.0 mmol) N,N-dimethylmethylenimmonium iodide and the reaction was stirred overnight at room temperature. The reaction mixture was poured into saturated sodium bicarbonate solution and extracted with dichloromethane. The organic layers were dried over magnesium sulphate and concentrated in vacuo. The residue (11.4 g) was suspended in toluene (500 ml) and 9.3 g (54.0 mmol) acetophenone pyrrolidine enamine were added. The suspension was heated at 100° C. for 7 h and after cooling to room temperature, the solvent was removed in vacuo. The residue was purified by column chromatography on silica gel (dichloromethane/methanol=30:1) to afford 6.8 g (50%) of the title compound as a green foam.

X. 7-Hydroxy-2-isopropyl-3-methyl-6-(3-oxo-3-phenyl-propyl)-3H-benzimidazole-5-carboxylic Acid Dimethylamide A solution of 3.2 g (10.5 mmol) 7-hydroxy-2-isopropyl-3-methyl-3H-benzimidazole-5-carboxylic acid dimethylamide in dry dichloromethane (100 ml) was treated with 2.1 g (11.5 mmol) N,N-dimethyl-methylenimmonium iodide and the reaction was stirred at mom temperature for 3.5 h. The reaction mixture was poured into saturated sodium bicarbonate solution and extracted with dichloromethane. The organic layers were dried over magnesium sulphate and concentrated in vacuo. The residue (3.4 g) was suspended in toluene (70 ml) and 2.7 g (11.5 mmol) acetophenone pyrrolidine enamine were added. The suspension was heated at 100° C. overnight and after cooling to room temperature, the solvent was removed in vacuo. The residue was purified by column chromatography on silica gel (dichloromethane/methanol=96.4) to afford 1.4 g (34%) of the title compound as a brown foam.

Y. 7-Hydroxy-3-methyl-6-(3-oxo-3-phenyl-propyl)-2-trifluoromethyl-3H-benzimidazole-5-carboxylic Acid Dimethylamide A suspension of 6.8 g (23.7 mmol) 7-hydroxy-3-methyl-2-trifluoromethyl-3H-benzimidazole-5-carboxylic acid dimethylamide in dry dichloromethane (350 ml) was treated with 5.7 g (30.8 mmol) N,N-dimethyl-methylenimmonium iodide and the reaction was stirred overnight at room temperature. The reaction mixture was poured into water and extracted with dichloromethane. The organic layers were dried over magnesium sulphate and concentrated in vacuo. The residue (9.0 g) was suspended in toluene (100 ml) and 6.8 g (39.1 mmol) acetophenone pyrrolidine enamine were added. The suspension was heated at 100° C. for 5 h and after cooling to room temperature, the solvent was removed in vacuo. 3.0 g (30%) of the title compound were isolated as a brown foam.

Z. 2-Cyclopropyl-7-hydroxy-3-methyl-3H-benzimidazol-5-carboxylic Acid Dimethylamide A solution of 15.4 g (42.0 mmol) 7-benzyloxy-2-cyclopropyl-3-methyl-3H-benzimidazole-5-carboxylic acid dimethylamide in 200 ml ethanol and 3.6 ml acetic acid was hydrogenated over 3.4 g 10% Pd/C in autoclave (5 bar $H_2$) at 50° C. for 16 h. The catalyst was filtered off and the filtrate was concentrated in vacuo. The residue was crystallized from diisopropyl ether to afford 10 g (92%) of the title compound as a white solid.

NMR (d6-DMSO): δ=1.05 (m, 4H), 2.22 (m, 1H), 2.98 (s, 6H, N(C$\underline{H}_3$)$_2$), 3.79 (s, 3H, NC$\underline{H}_3$), 6.52 (s, 1H), 6.96 (s, 1H), 9.7 (broad, 1H, OH).

AA. 7-Hydroxy-3-methyl-2-trifluoromethyl-3H-benzimidazole-5-carboxylic Acid Dimethylamide A solution of 9.0 g (23.8 mmol) 7-benzyloxy-3-methyl-2-trifluoromethyl-3H-benzimidazole-5-carboxylic acid dimethylamide and 1.2 ml acetic acid in 300 ml ethanol-tetrahydrofuran (1:1) was hydrogenated over 1.1 g 10% Pd/C in autoclave (5 bar $H_2$) at 50° C. for 16 h. The catalyst was filtered off and the filtrate concentrated in vacuo to afford 6.9 g (100%) of the title compound as a white solid. m.p. 243-244° C.

AB. 7-Hydroxy-2-isopropyl-3-methyl-3H-benzimidazole-5-carboxylic Acid Dimethylamide A solution of 3.6 g (10.3 mmol) 7-benzyloxy-2-isopropyl-3-methyl-3H-benzimidazole-5-carboxylic acid dimethylamide and 900 μl acetic acid in 70 ml methanol was hydrogenated over 885 mg 10% Pd/C in autoclave (5 bar $H_2$) at 50° C. for 15 h. The catalyst was filtered off and the filtrate was concentrated in vacuo to afford 3.2 g (100%) of the title compound as a grey wax.

AC. 7-Benzyloxy-2-isopropyl-3-methyl-3H-benzimidazole-5-carboxylic Acid Dimethylamide 5.6 g (15.5 mmol) 4-Benzyloxy-6-bromo-2-isopropyl-1-methyl-1H-benzimidazole, 2.4 g (3.3 mmol) triphenylphosphine, 521 mg (2.3 mmol) palladium(II) acetate and 78.5 ml (155 mmol) dimethylamine (2 M in THF) were transferred to an autoclave and carbonylated (6 bar $CO_2$) at 120° C. for 3 h. The catalyst was filtered off and the filtrate was concentrated in vacuo. Purification of the residue by column chromatography on silica gel (petroleum ether/ethyl acetate=1:5) afforded 3.8 g (70%) of the title compound as a yellow wax.

AD. 7-Benzyloxy-3-methyl-2-trifluoromethyl-3H-benzimidazole-5-carboxylic Acid Dimethylamide 15.8 g (41.0 mmol) 4-Benzyloxy-6-bromo-1-methyl-2-trifluoromethyl-1H-benzimidazole, 6.4 g (24.6 mmol) triphenylphosphine, 1.4 g (6.2 mmol) palladium(II) acetate and 205 ml (410 mmol) dimethylamine (2 M in THF) were transferred to an autoclave and carbonylated (6 bar $CO_2$) at 120° C. for 16 h. The catalyst was filtered off and the filtrate was concentrated in vacuo. Purification of the residue by column chromatography on silica gel (dichloromethane/methanol=50:1) afforded 9.3 g (62%) of the title compound as a white solid. m.p. 144°-146° C.

AE. 7-Benzyloxy-2-cyclopropyl-3-methyl-3-benzimidazole-5carboxylic Acid Dimethylamide 15.1 g (42.3 mmol) 4-Benzyloxy-6-bromo-2-cyclopropyl-1-methyl-1H-benzimidazole, 6.6 g (25.4 mmol) triphenylphosphine, 1.4 g (6.2 mmol) palladium(II) acetate, 169 ml (338 mmol) dimethylamine (2 M in THF) in 250 ml tetrahydrofuran were transferred to an autoclave and carbonylated (6 bar $CO_2$) at 120° C. for 16 h. The catalyst was filtered off and the filtrate was concentrated in vacuo. Purification of the residue by column chromatography on silica gel (dichloromethane/methanol=40:1) afforded 15.4 g (100%) of the title compound as a yellow oil.

AF. 4-Benzyloxy-6-bromo-2-isopropyl-1-methyl-1H-benzimidazole

A suspension of 12.9 g (33.1 mmol) N-(benzyloxy-bromo-dimethylamino-phenyl)-isobutyramide in 27.1 ml phosphoryl chloride was heated at 90° C. for 4 h. After cooling to room temperature, the reaction mixture was diluted with dichloromethane and cooled to 0° C. The pH was adjusted to pH=8 by cautiously adding 10N sodium hydroxide solution, the organic layer was separated, dried over magnesium sulphate and concentrated in vacuo. The residue was purified by column chromatography on silica gel (dichloromethane/methanol=80:1) to afford 5.7 g (48%) of the title compound as a beige solid. m.p. 132°-133° C.

AG. 4-Benzyloxy-6-bromo-1-methyl-2-trifluoromethyl-1H-benzimidazole

A solution of 40 g (107.8 mmol) 4-benzyloxy-6-bromo-2-trifluoromethyl-1H-benzimidazole in acetone (600 ml) was treated with 44.7 g (323.4 mmol) potassium carbonate and the reaction was refluxed for 1 h. 13.4 ml Methyl iodide were added and the mixture was stirred for 2 h. After cooling to room temperature, the precipitate was filtered off and the filtrate was concentrated in vacuo. Purification of the residue by column chromatography on silica gel (petroleum ether/ethyl acetate=15:1) afforded 13.2 g (32%) of the title compound as a white solid. m.p. 141°-142° C.

AH. N-(Benzyloxy-bromo-dimethylamino-phenyl) isobutyramide

A suspension of 12.7 g (35 mmol) N-(2-amino-6-benzyloxy-4-bromo-phenyl)-isobutyramide in methanol (400 ml) and 83 ml (1.05 Mol) formaldehyde (37% in water) was acidified with hydrogen chloride to give a clear solution. 3.3 g (52.5 mmol) Sodium cyanoborohydride were added and the reaction was stirred at room temperature for 3 h. The mixture was poured into water and neutralized with 10 N sodium hydroxide solution. The precipitate was filtered off and dried in vacuo at 40° C. to afford 13.9 g (100%) of the tile compound as a white powder. m.p. 197°-198° C.

AI. 4-Benzyloxy-6-bromo-2-trifluoromethyl-1H-benzimidazole

To a suspension of 26.1 g (67.4 mmol) 4benzyloxy-6-bromo-2-trifluoromethyl-benzimidazol-1-ol in chloroform (260 ml) were cautiously added 19 ml (202 mmol) phosphorus tribromide and the reaction was refluxed for 4 h. After cooling to room temperature, the reaction mixture was poured into water (600 ml), neutralized with sodium bicarbonate solution and extracted with dichloromethane. The organic layers were dried over magnesium sulphate and concentrated in vacuo to afford 19.8 g (79%) of the title compound as a brown oil.

AJ. N-(2-Amino-6-benzyloxy-4-bromo-phenyl)-isobutyramide

A suspension of 25.2 g (64.3 mmol) N-(2benzyloxy-4-bromo-6-nitro-phenyl)-isobutyramide, 6.3 g (38.5 mmol) iron(III) chloride and 15.7 g activated charcoal in 600 ml methanol was heated to 70° C. 31.3 ml (643 mmol). Hydrazine hydrate were added dropwise and the reaction mixture was refluxed for 90 min. After cooling to room temperature the reaction was filtered through celite, the filter cake washed with dichloromethane/methanol and the filtrate concentrated in vacuo. The residue was dried in vacuo at 40° C. to afford 13.0 g (56%) of the title compound as a white solid. m.p. 214°-215° C.

AK. 4-Benzyloxy-6-bromo-2-trifluoromethyl-benzimidazol-1-ol

A suspension of 56.6 g (135 mmol) N-(2-benzyloxy-4-bromonitro-phenyl)-2,2,2-trifluoro-acetamide in 2 L ethanol was hydrogenated over Raney-Nickel (1 bar $H_2$) for 3 h. The reaction was filtered through celite and the filtrate was concentrated in vacuo. The residue was purified by column chromatography on silica gel (petroleum ether/ethyl acetate=5:1) to afford 30.6 g (58%) of the title compound as a beige solid.

m.p. 211°-214° C.

AL. N-(2-Benzyloxy-6-bromo-6-nitro-phenyl)-isobutyramide

A suspension of 20 g (62 mmol) 2-benzyloxy-4-bromo-6-nitro-aniline in 120 ml isobutyric anhydride and 1.9 ml (50.4 mmol) methanesulphonic acid was heated at 120° C. for 2.5 h. After cooling to room temperature, the reaction mixture was poured into water, neutralized with 10 N sodium hydroxide solution and extracted with dichloromethane. The organic layers were dried over magnesium sulphate and concentrated in vacuo. The residue was crystallized from diisopropyl ether to afford 1.6 g (7%) of the title compound as a white solid. m.p. 197°-198° C.

AM. N-(2-Benzyloxy-4-bromo-6-nitro-phenyl)-2,2,2-trifluoro-acetamide

A solution of 50 g (155 mmol) 2-benzyloxy-4-bromo-6-nitro-aniline in 400 ml dioxane was treated with 44 ml (310 mmol) trifluoroacetic anhydride and transferred to an autoclave. The reaction was heated at 120° C. for 3 h and after cooling to room temperature, the solvent was removed in vacuo. The residue was crystallized from ethanol to afford 53.6 g (83%) of the title compound as a grey solid. m.p. 146°-147° C.

AN. 4-Benzyloxy-6-bromo-1-methoxymethyl-2-methyl-1H-benzimidazole 2.0 g (6.3 mmol) 4-Benzyloxy-6-bromo-2-methyl-1H-benzimidazole were solved in dimethylformamide (10 ml) and the solution was cooled to 0° C. 151 mg (6.5 mmol) sodium hydride (60%) were added in portions and the reaction was stirred for 20 min. 435 µl (6.3 mmol) 1-Chloro-1-methoxy-methane were added and the reaction was stirred at 0° C. After 2 h the mixture was poured into water (200 ml) and extracted with ethyl acetate. The organic layers were dried over magnesium sulphate and concentrated in vacuo. The residue was purified by column chromatography on silica gel (toluene/dioxane=6:1) to afford 0.6 g (26%) of the title compound as a yellow oil.

AO. 7-Benzyloxy-3-methoxymethyl-2-methyl-3H-benzimidazole-5-carboxylic Acid Dimethylamide 10.6 g (29.3 mmol) 4-Benzyloxy-bromo-1-methoxymethyl-2-methyl-1H-benzimidazole, 4.6 g (17.6 mmol) triphenylphosphine, 1.0 g (4.3 mmol) palladium(II) acetate, 148 ml (293 mmol) dimethylamine (2 M in THF) in 50 ml tetrahydrofuran were transferred to an autoclave and carbonylated (6 bar $CO_2$) at 120° C. for 16 h. The catalyst was filtered off and the filtrate was concentrated in vacuo. The purification of the residue by column chromatography on silica gel (dichloromethane/methanol=20:1) afforded 4.9 g (50%) of the title compound as a yellow oil.

AP. 7-Hydroxy-3-methoxymethyl-2-methyl-3H-benzimidazole-5-carboxylic Acid Dimethylamide A solution of 1.8 g (5.0 mmol) 7-benzyloxy-3-methoxymethyl-2-methyl-3H-benzimidazole-5-carboxylic acid dimethylamide and 270 µl acetic acid in 150 ml ethanol was hydrogenated over 240 mg 10% Pd/C in autoclave (5 bar $H_2$) at 50° C. for 18 h. The catalyst was filtered off and the filtrate was concentrated in vacuo and crystallized from ethyl acetate-petroleum ether to afford 0.8 g (62%) of the title compound as a white solid. m.p. 173°-183° C.

AG. 6-Dimethylaminomethyl-7-hydroxy-3-methoxymethyl-1H-benzimidazole-5-carboxylic Acid Dimethylamide Hydrogen Iodide A solution of 1.0 g (3.8 mmol) 7-hydroxy-3-methoxymethyl-2-methyl-3H-benzimidazole-5-carboxylic acid dimethylamide in dry dichloromethane (30 ml) was treated with 0.7 g (4.2 mmol) N,N-dimethyl-methylenimmonium iodide and the reaction was stirred 24 h at room temperature. The reaction mixture was poured into water and extracted with dichloromethane (3×20 ml). The organic layers were dried over magnesium sulphate and concentrated in vacuo. The residue was crystallized from diisopropyl ether to afford 1.1 g (92%) of the title compound as a white solid. m.p. 146°-147° C.

AR. 7-Hydroxy-3-methoxymethyl-2-methyl-6-(3-oxo-3-phenyl)-1H-benzimidazole-5-carboxylic Acid Dimethylamide 1.1 g (3.4 mmol) 6-Dimethylaminomethyl-7-hydroxy-3-methoxymethyl-1H-benzimidazole-5-carboxylic acid dimethylamide hydrogen iodide were suspended in toluene (25 ml) and 0.8 g (4.7 mmol) acetophenone pyrrolidine enamine were added. The suspension was heated at 100° C. for 4 h and after cooling to room temperature, the solvent was removed in vacuo. The residue was purified by column chromatography on silica gel (dichloromethane/methanol=30:1) and crystallized from ethyl acetate to afford 0.3 g (27%) of the title compound as a brown solid. m.p. 210°-213° C.

AS. 7-Hydroxy-6-(3-hydroxy-3-phenyl-propyl)-2,3-dimethybenzimidazole-5-carboxylic Acid Dimethylamide A suspension of 0.2 g (0.6 mmol) 7-hydroxy-3-methoxymethyl-2-methyl-6-(3-oxo-3-phenyl)-1H-benzoimidazole-5-carboxylic acid dimethylamide in ethanol (5 ml) was treated with 30 mg (0.8 mmol) sodium borohydride and the reaction was stirred at room temperature for 3 h. A saturated ammonium chloride solution was added and the reaction was extracted with dichloromethane. The organic layers were dried over magnesium sulphate and concentrated in vacuo. The residue afforded 0.2 g (80%) of the title compound as a brown solid. m.p. 216°-218° C.

AT. N-(7-Benzyloxy-2,3-dimethyl-3H-benzimidazol-5-yl)-acetamide

A solution of 10 g (30.2 mmol) 4-benzyloxy-6-bromo-1,2-dimethyl-1H-benzimidazole, 2.1 g (36.2 mmol) acetamide, 524 mg (0.9 mmol) xantphos, 13.7 g (42.3 mmol) cesium carbonate and 276 mg (0.3 mmol) $Pd_2(dba)_3$ in 60 ml dioxane was stirred at 100° C. for 20 h. The reaction mixture was cooled to room temperature and poured into dichloromethane. The precipitate was filtered off and the filtrate was concentrated in vacuo. The residue was purified by column chromatography on silica gel (toluene/dioxane=2:1) to afford 5.8 g (62%) of the title compound as a white foam.

AU. N-(7-Benzyloxy-2,3-dimethyl-3H-benzimidazol-5-yl)-N-methyl-acetamide

To a suspension of 5.8 g (18.8 mmol) N-(7-benzyloxy-2,3-dimethy-3H-benzimidazol-5-yl)-acetamide in tetrahydrofuran (200 ml) were added 1.3 ml (20.5 mmol) methyl iodide and 0.74 g (20.5 mmol) sodium hydride (60%) in portions. The reaction was stirred at room temperature for 1 h and then poured into water (100 ml) and extracted with ethyl acetate (4×50 ml). The organic layers were dried over magnesium sulphate and concentrated in vacuo. The residue afforded 6.0 g (99%) of the title compound as ochre solid. m.p. 144°-149° C.

AV. N-(7-Hydroxy-2,3-dimethy-3H-benzimidazol-5-yl)-N-methyl-acetamide

A solution of 3.1 g (18.9 mmol) N-(7-benzyloxy-2,3-dimethy-3H-benzimidazol-5-yl)-N-methyl-acetamide and 1.2 ml acetic acid in 600 ml ethanol was hydrogenated over 1.2 g 10%. Pd/C in an autoclave (5 bar $H_2$) at 50° C. for 18 h. The catalyst was filtered off and the filtrate was concentrated in vacuo to afford 4.5 g (100%) of the title compound as a yellow solid.

$^1$H-NMR (d6-DMSO): δ=1.8 (s, 3H, $CH_3$), 2.52 (s, 3H, $CH_3$), 3.11 (a, 3H, $CH_3$), 3.68 (s, 3H, $CH_3$), 6.39 (s, 1H, Ar), 6.91 (s, 1H, Ar), 10.0 (broad, 1H, OH).

AW. N-(6-Dimethylaminomethyl-7-hydroxy-2,3-dimethyl-3H-benzimidazol-5yl)-N-methyl-acetamide A suspension of 4.7 g (18.9 mmol) N-(7-benzyloxy-2,3-dimethy-3H-benzimidazol-5-yl)-N-methyl-acetamide in dry dichloromethane (200 ml) was treated with 4.5 g (24.6 mmol) N,N-dimethylmethylenimmonium iodide and the reaction was stirred overnight at room temperature. The reaction mixture was poured into water, neutralized with sat. sodium bicarbonate solution and extracted with dichloromethane (2×20 ml). The organic layers were dried over magnesium sulphate and concentrated in vacuo. The residue afforded 2.2 g (41%) of the title compound as a white solid. m.p. 181°-184° C.

AX. N-[7-Hydroxy-2,3-dimethyl-6-(3-oxo-3-phenyl-propyl)-3H-benzimidazol-5-yl]-N-methyl-acetamide 2.2 g (7.6 mmol) N-(6-Dimethylaminomethyl-7-hydroxy-2,3-dimethyl-3H-benzimidazol-5-yl)-N-methyl-acetoamide were suspended in toluene (100 ml) and 2.6 g (15.3 mmol) acetophenone pyrrolidine enamine were added. The suspension was heated at 100° C. for 8 h and after cooling to room temperature, the solvent was removed in vacuo. The residue was purified by column chromatography on silica gel (dichloromethane/methanol=14:1) to afford 0.83 g (30%) of the title compound as a beige solid. m.p. 249°-251° C.

AY. N-[7-Hydroxy-6-(3-hydroxy-3-phenyl-propyl)-2,3-dimethyl-3H-benzimidazol-5yl]-N-methyl-acetamide A suspension of 0.8 g (2.2 mmol) N-[7-hydroxy-2,3-dimethyl-6-(3-oxo-3-phenyl-propyl)-3H-benzimidazol-5-yl]-N-methyl-acetamide in ethanol (200 ml) was treated with 100 mg (3.6 mmol) sodium borohydride and the reaction was stirred at room temperature for 1 h. A saturated ammonium chloride solution was added and the reaction was extracted with ethyl acetate (3×20 ml). The organic layers were dried over magnesium sulphate and concentrated in vacuo. The residue afforded 0.77 g (95%) of the title compound as a beige foam.

AZ. N-(2-Benzyloxy-4-bromo-6nitro-phenyl)-N-propionyl-proplonamide

To a suspension of 23 g (0.07 Mol) 2-benzyloxy-4-bromo-6-nitro-phenyl amine in propionic anhydride (55 ml) were added 3.7 g methanesulphonic acid and the reaction was heated at 125° C. for 2 h. After cooling to room temperature, the reaction mixture was poured into water (200 ml) and extracted with dichloromethane. The organic layers were dried over magnesium sulphate and concentrated in vacuo. The residue was purified by chromatography on silica gel (dichloromethane) and crystallized from petroleum ether to afford 19 g (62%) of the title compound as a red solid. m.p. 90°-92° C.

BA. N-(2-Amino-6-benzyloxy-4-bromo-phenyl)-propionamide

A solution of 22 g (48.5 mmol) N-(2-benzyloxy-4-bromo-6-nitro-phenyl)-propionyl-propionamide, 4.9 g (30 mmol) iron(III) chloride and 7.2 g activated charcoal in 180 ml methanol was heated to 70° C. 23.8 ml (490 mmol) Hydrazine hydrate were added dropwise and the reaction mixture was refluxed for 90 min. After cooling to room temperature, the reaction was filtered through celite, the filter cake washed with dichloromethane, the filtrate reduced in volume and poured into water. The precipitate was filtered and washed with diethyl ether to afford 19 g (89%) of the title compound as a white solid.

m.p. 198°-201° C.

BB. N-(Benzyloxy-bromo-dimethylamino-phenyl) propionamide

A suspension of 17 g (48.6 mmol) N-(2-amino-6-benzyloxy-4-bromo-phenyl)propionamide in methanol (140 ml) and 116 ml (1.05 Mol) formaldehyde (37% in water) was acidified with hydrogen chloride (3.8 ml) to give a dear solution. 4.6 g (72.9 mmol) Sodium cyanoborohydride were added and the reaction was stirred at room temperature for 1 h. The mixture was poured into water, the precipitate was filtered off and recrystallized from diethyl ether to afford 14.8 g (81%) of the title compound as a white solid.

m.p. 176°-177° C.

BC. 4-Benzyloxy-6-bromo-2-ethyl-1-methyl-1H-benzimidazole

A suspension of 14.8 g (39.2 mmol) N-(benzyloxy-bromo-dimethylamino-phenyl)-propionamide in 35.7 ml phosphoryl chloride was heated at 70° C. for 1 h. After cooling to room temperature, the reaction mixture was diluted with dichloromethane and cooled to 0° C. The pH was adjusted to pH=8 by cautiously adding 10N sodium hydroxide solution, the organic layer was separated, dried over magnesium sulphate and concentrated in vacuo. The residue was crystallized from diethyl ether to afford 10.1 g (75%) of the title compound as a white solid. m.p. 111°-115° C.

BD. 7-Benzyloxy-2-ethyl-3-methyl-3H-benzimidazole-5-carboxylic Acid Dimethylamide 10 g (29 mmol) 4-Benzyloxy-6-bromo-2-ethyl-1-methyl-1H-benzimidazole, 4.6 g (17.4 mmol) triphenylphosphine, 1.0 g (4.3 mmol) palladium(II) acetate in 145 ml (290 mmol) dimethylamine (2 M in THF) were transferred to an autoclave and carbonylated (6 bar $CO_2$) at 120° C. for 24 h. The catalyst was filtered off and the filtrate was concentrated in vacuo. Purification of the residue by column chromatography on silica gel (dichloromethane/methanol=93:7) and crystallization from diethyl ether afforded 11.3 g (91%) of the title compound as white crystals. m.p. 104°-108° C.

BE. 2-Ethyl-7-hydroxy-3-methyl-3H-benzimidazole-5-carboxylic Acid Dimethylamide A solution of 10.9 g (26.6 mmol) 7-benzyloxy-2-ethyl-3-methyl-3H-benzimidazole-5-carboxylic acid dimethylamide and 1.8 ml acetic acid in 160 ml ethanol was hydrogenated over 1.7 g 10% Pd/C in autoclave (5 bar $H_2$) at 50° C. for 18 h. The catalyst was filtered off and the filtrate was concentrated in vacuo. The residue was crystallized from acetone to afford 7 g (91%) of the title compound as a white solid. m.p. 193°-199° C.

BF. 6-Dimethylaminomethyl-2-ethyl-7-hydroxy-3-methyl-3H-benzimidazole-5carboxylic Acid Dimethylamide A solution of 7.0 g (25 mmol) 2-ethyl-7-hydroxy-3-methyl-3H-benzimidazole-5-carboxylic acid dimethylamide in dry dichloromethane (200 ml) was treated with 5.9 g (24.6 mmol) N,N-dimethyl-methylenimmonium iodide and the reaction was stirred overnight at room temperature. The reaction mixture was poured into water, neutralized with saturated sodium bicarbonate solution and extracted with dichloromethane (3×100 ml). The organic layers were dried over magnesium sulphate and concentrated in vacuo. The residue afforded 6.6 g (88%) of the title compound as a yellow powder.
m.p. 183°-185° C.

BG. 2-Ethyl-7-hydroxy-6-(3-oxo-3-phenyl-propy)-3-methyl-3H-benzimidazole-5-carboxylic Acid Dimethylamide 6.6 g (21.6 mmol) 6-Dimethylaminomethyl-2-ethyl-7-hydroxy-3-methyl-3H-benzimidazole-5-carboxylic acid dimethylamide were suspended in toluene (100 ml) and 5.7 g (15.3 mmol) acetophenone pyrrolidine enamine were added. The suspension was heated at 100° C. for 2.5 h and after cooling to room temperature, the solvent was removed in vacuo. The residue was purified by column chromatography on silica gel (dichloromethane/methanol=14:1) and crystallized from acetone-diethyl ether to afford 1.6 g (19%) of the title compound as a white solid. m.p. 177°-180° C.

BH. 2-Ethyl-7-hydroxy-(3-hydroxy-3-phenyl-propyl)-3-methyl-3H-benzimidazole-5-carboxylic Acid Dimethylamide A suspension of 1.5 g (4.0 mmol) 2-ethyl-7-hydroxy-3-methyl-6-(3-oxo-3-phenyl-propyl)-3H-benzimidazole-5-carboxylic acid dimethylamide in ethanol (50 ml) was treated with 0.2 g (4.8 mmol) sodium borohydride and the reaction was stirred at room temperature for 1 h. A saturated ammonium chloride solution was added and the reaction was extracted dichloromethane (4×75 ml). The organic layers were dried over magnesium sulphate and concentrated in vacuo. The residue afforded 1.2 g (80%) of the title compound as a white solid. m.p. 121°-124° C.

BI. 7-Hydroxy-6-(2-hydroxy-3-phenyl-propyl)-2-methyl-3-(2-trimethylsilanyl-ethoxymethyl)-3H-benzimidazole-5-carboxylic Acid Dimethylamide A suspension of 0.7 g (1.4 mmol) 7-hydroxy-2-methyl-6-(3-oxo-3-phenyl-propyl)-3-(2 (trimethylsilanyl-ethoxymethyl)-3H-benzimidazole-5-carboxylic acid dimethylamide in 20 ml ethanol was treated with 0.7 g (1.7 mmol) sodium borohydride and the reaction was stirred at room temperature for 1 h. A satured ammonium chloride solution was added and the reaction was stirred for further 30 min. The reaction mixture was poured into water and extracted with dichloromethane (3×20 ml). The organic layers were dried over magnesium sulphate and concentrated in vacuo to afford 0.7 g (100%) of the title compound as a white foam.

BJ. 7-Hydroxy-2-methyl-6-(3-oxo-3-phenyl-propyl)-3-(2-trimethylsilanyl-ethoxymethyl)-3H-benzimidazole-5-carboxylic Acid Dimethylamide A solution of 2.6 g (7.3 mmol) 7-hydroxy-2-methyl-3-(2-trimethylsilanyl-ethoxymethyl)-3H-benzo-imidazole-5-carboxylic acid dimethylamide in 160 ml dichloromethane was treated with 1.6 g (8.8 mmol) N,N-dimethylmethylenimmonium iodide and the reaction was stirred at room temperature for 2.5 h. The solvent was removed in vacuo, the residue was suspended in 30 ml toluene and the suspension was treated with 0.90 g (5.7 mmol) acetophenone pyrrolidine enamine. After heating at 100° C. for 3 h, the reaction mixture was concentrated in vacuo. The residue was purified by column chromatography on silica gel (ethyl acetate/petroleum ether=5:1) to afford 0.71 g (20%) of the title compound as a beige solid. m.p. 192°-194° C.

BK. 7-Hydroxy-2-methyl-(2-trimethylsilanyl-ethoxymethyl)-3H-benzimidazole-5-carboxylic Acid Dimethylamide A solution of 3.6 g (8.3 mmol) 7-benzyloxy-2-methyl-3-(2-trimethylsilanyl-ethoxymethyl)-3H-benzo-imidazole-5-carboxylic acid dimethylamide in 400 ml ethanol was hydrogenated over 365 mg 10% Pd/C at room temperature for 1 h. The catalyst was filtered off and the filtrate was concentrated in vacuo. The residue was crystallized from diisopropyl ether to afford 2.6 g (89%) of the title compound as a while solid. m.p. 150°-151° C.

BL. 7-Benzyloxy-2-methyl-3-(2-trimethylsilanyl-ethoxymethyl)-3H-benzimidazole-5-carboxylic Acid Dimethylamide 5.8 g (13 mmol) 4-Benzyloxy-6-bromo-2-methyl-1-(2-trimethylsilanyl-ethoxymethyl)-1H-benzimidazole, 1.3 g (5.2 mmol) triphenylphosphine, 0.4 g (1.9 mmol) palladium (II) acetate and 80 ml (160 mmol) dimethylamine (2M in THF) were transferred to an autoclave and carbonylated (6 bar $CO_2$) at 120° C. for 16 h. The catalyst was filtered off and the filtrate was concentrated in vacuo. The crystallization of the residue from diisopropyl ether afforded 3.7 g (65%) of the title compound as a white solid.
m.p. 142°-146° C.

BM. 4-Benzyloxy-6-bromo-2-methyl-1-(2-trimethylsilanyl-ethoxymethyl)-1H-benzimidazole 18.6 g (58.6 mmol) 4-Benzyloxy-6-bromo-2-methyl-1H-benzimidazole and 9 ml (70.3 mmol) triethyl-amine were suspended in 370 ml dichloromethane and 13.9 ml (70.3 mmol) (2-chloromethoxy-ethyl)-trimethylsilane were added dropwise. The reaction was stirred at room temperature for 3 h, poured into water (400 ml) and extracted with dichloromethane (3×100 ml). The organic layers were dried over magnesium sulphate and concentrated in vacuo. The residue was purified by column chromatography on silica gel (toluene/dioxane=9:1) to afford 5.9 g (23%) of the title compound as a beige solid. m.p. 94°-95° C.

BN. 7-Hydroxy-6-((R3)-3-hydroxy-3-phenyl-propyl-2,3-dimethyl-3H-benzimidazol-5-carboxylic Acid Dimethylamide In a flame-dried flask filled with argon, 0.8 g (2.2 mmol) 7-hydroxy-2,3-dimethyl-6-(3-oxo-3-phenylpropyl)-3H-benzoimidazole-5-carboxylic acid dimethylamide were dissolved in 130 ml dry isopropanol and degassed with argon. 295 mg (2.2 mmol) tert-Butylate and 120 mg (5 mol-%) $RuCl_2[(S)-BINAP][(S)-DAIPEN]$ were added and the solution was transferred to an autoclave and hydrogenated at room temperature for 18 h (40 bar). The reaction mixture was poured into a satured ammonium chloride solution (80 ml) and extracted with ethyl acetate (3×20 ml). The organic layers were dried over magnesium sulphate and concentrated in vacuo. The residue was purified by column chromatography on silica gel (dichloromethane/methanol=9:1) to afford 0.4 g (50%) of the title compound as a green solid. m.p. 262°-264° C. $[\alpha]_D=+62°$ (c=0.2 in $CHCl_3$).

Commercial Utility

The compounds of the formulae 1, 1a and 2 and their pharmacologically acceptable salts (=active compounds according to the invention) have valuable pharmacological properties which make them commercially utilizable. In particular, they exhibit marked inhibition of gastric acid secretion and an excellent gastric and intestinal protective action in warm-blooded animals, in particular humans. In this connection, the active compounds according to the invention are distinguished by a high selectivity of action, an advantageous duration of action, a particularly good enteral activity, the absence of significant side effects and a large therapeutic range.

"Gastric and intestinal protection" in this connection is understood as meaning the prevention and treatment of gastrointestinal diseases, in particular of gastrointestinal inflammatory diseases and lesions (such as, for example, gastric ulcer, peptic ulcer, including peptic ulcer bleeding, duodenal ulcer, gastritis, hyperacidic or medicament-related functional dyspepsia), which can be caused, for example, by microorganisms (e.g. *Helicobacter pylori*), bacterial toxins, medicaments (e.g. certain antiinflammatories and antirheumatics, such as NSAIDs and COX-inhibitors), chemicals (e.g. ethanol) gastric acid or stress situations. "Gastric and intestinal protection" is understood to include, according to general knowledge, gastroesophageal reflux disease (GERD), the symptoms of which include, but are not limited to, heartburn and/or acid regurgitation.

In their excellent properties, the active compounds according to the invention surprisingly prove to be clearly superior to the compounds known from the prior art in various models in which the antiulcerogenic and the antisecretory properties are determined. On account of these properties, the active compounds according to the invention are outstandingly suitable for use in human and veterinary medicine, where they are used, in particular, for the treatment and/or prophylaxis of disorders of the stomach and/or intestine.

A further subject of the invention are therefore the active compounds according to the invention for use in the treatment and/or prophylaxis of the abovementioned diseases.

The invention likewise includes the use of the active compounds according to the invention for the production of medicaments which are employed for the treatment and/or prophylaxis of the abovementioned diseases.

The invention furthermore includes the use of the active compounds according to the invention for the treatment and/or prophylaxis of the abovementioned diseases.

A further subject of the invention are medicaments which comprise one or more active compounds according to the invention.

The medicaments are prepared by processes which are known per se and familiar to the person skilled in the art. As medicaments, the active compounds according to the invention (=active compounds) are either employed as such, or preferably in combination with suitable pharmaceutical auxiliaries or excipients in the form of tablets, coated tablets, capsules, suppositories, patches (e.g. as TTS), emulsions, suspensions or solutions, the active compound content advantageously being between 0.1 and 95% and it being possible to obtain a pharmaceutical administration form exactly adapted to the active compound and/or to the desired onset and/or duration of action (e.g. a sustained-release form or an enteric form) by means of the appropriate selection of the auxiliaries and excipients.

The auxiliaries and excipients which are suitable for the desired pharmaceutical formulations are known to the person skilled in the art on the basis of his/her expert knowledge. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, d appropriate in the form of several, preferably 1 to 4, individual doses to achieve the desired result. In the case of a parenteral treatment, similar or (in particular in the case of the intravenous administration of the active compounds), as a rule, lower doses can be used. The establishment of the optimal dose and manner of administration of the active compounds necessary in each case can easily be carried out by any person skilled in the art on the basis of his/her expert knowledge.

If the active compounds according to the invention and/or their salts are to be used for the treatment of the abovementioned diseases, the pharmaceutical preparations can also contain one or more pharmacologically active constituents of other groups of medicaments, for example: tranquilizers (for example from the group of the benzodiazepines, for example diazepam), spasmolytics (for example, bietamiverine or camylofine), anticholinergics (for example, oxyphencyclimine or phencarbamide), local anesthetics, (for example, tetracaine or procaine), and, if appropriate, also enzymes, vitamins or amino acids.

To be emphasized in this connection is in particular the combination of the active compounds according to the invention with pharmaceuticals which inhibit acid secretion, such as, for example, $H_2$ blockers (e.g. cimetidine, ranitidine), $H^+/K^+$ ATPase inhibitors (e.g. omeprazole, pantoprazole), or further with so-called peripheral anticholinergics (e.g. pirenzepine, telenzepine) and with gastrin antagonists with the aim of increasing the principal action in an additive or super-additive sense and/or of eliminating or of decreasing the side effects, or further the combination with antibacterially active substances (such as, for example, cephalosporins, tetracyclines, penicillins, macrolides, nitroimidazoles or alternatively bismuth salts) for the control of *Helicobacter pyiori*. Suitable antibacterial co-components which may be mentioned are, for example, meziocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (for example clarithromycin+metronidazole).

In view of their excellent gastric and intestinal protection action, the active compounds according to the invention are suited for a tree or fixed combination with those medicaments (e.g. certain antiinflammatories and antirheumatics, such as NSAIDs), which are known to have a certain ulcerogenic potency. In addition, the compounds of formula 1 are suited for a free or fixed combination with motility-modifying drugs.

Pharmacology the excellent gastric protective action and the gastric acid secretion-inhibiting action of the compounds according to the invention can be demonstrated in investigations on animal experimental models. The compounds according to the invention investigated in the model mentioned below have been provided with numbers which correspond to the numbers of these compounds in the examples.

Testing of the Secretion-inhibiting Action on the Perfused Rat Stomach

In Table A which follows, the influence of the compounds according to the invention on the pentagastrin-stimulated acid secretion of the perfused rat stomach after intraduodenal administration in vivo is shown.

TABLE A

| No. | Dose (μmol/kg) i.d. | Inhibition of acid secretion |
|---|---|---|
| 1 | 1 | >50% |
| 2 | 1 | >50% |
| 4 | 1 | >50% |
| 10 | 1 | >50% |
| 18 | 1 | >50% |
| 29 | 1 | >50% |
| 32 (8S) | 1 | >50% |
| 33 (8S) | 1 | >50% |

Methodology

The abdomen of anesthetized rats (CD rat, rat, female, 200-250 g; 1.5 g/kg l.m. urethane) was opened after tracheotomy by a median upper abdominal incision and a PVC catheter was fixed transorally in the esophagus and another via the pylorus such that the ends of the tubes just projected into the gastric lumen. The catheter leading from the pylorus led outward into the right abdominal wall through a side opening.

After thorough rinsing (about 50-100 ml), warm (37° C.) physiological NaCl solution was continuously passed through the stomach (0.5 ml/min, pH 6.8-6.9; Braun-Unita 1). The pH (pH meter 632, glass electrode EA 147; φ=5 mm, Metrohm) and, by titration with a freshly prepared 0.01N NaOH solution to pH 7 (Dosimat 665 Metrohm), the secreted HCl were determined in the effluent in each case collected at an interval of 15 minutes.

The gastric secretion was stimulated by continuous infusion of 1 μg/kg (=1.65 ml/h) of i.v. pentagastrin (left femoral vein) about 30 min after the end of the operation (i.e. after determination of 2 preliminary fractions). The substances to be tested were administered intraduodenally in a 2.5 ml/kg liquid volume 60 min after the start of the continuous pentagastrin infusion.

The body temperature of the animals was kept at a constant 37.9-38° C. by infrared irradiation and heat pads (automatic, stepless control by means of a rectal temperature sensor).

The invention claimed is:
1. A compound of formula 1,

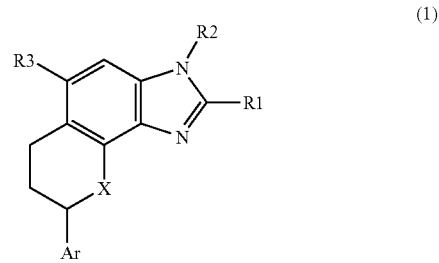

in which
Rb 1 is hydrogen, halogen, hydroxyl, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl, hydroxy-1-4C-alkyl or mono- or di-1-4C-alkylamino,
R2 is hydrogen, 1-4C-alkyl, 1-4C-alkoxy, 1-4C-alkoxy-1-4C-alkyl, aryl, 3-7C-cycloalkyl, 3-7C-cycloalkyl-1-4C-alkyl, 1-4C-alkoxycarbonyl, mono- or di-1-4C-alkylamino-1-4C-alkylcarbonyl, hydroxy-1-4C-alkyl, fluoro-2-4C-alkyl,
R3 is hydrogen, halogen, fluoro-1-4C-alkyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl, 1-4C-alkoxy-1-4C-alkoxy, 1-4C-alkylcarbonyamino, 1-4C-alkylcarbonyl-N-1-4C-alkylamino, 1-4C-alkoxy-1-4C-alkylcarbonylamino or the group —CO—NR31R32, where
R31 is hydrogen, hydroxyl, 1-7C-alkyl, 3-7C-cycloalkyl, hydroxy-1-4C-alkyl or 1-4C-alkoxy-1-4C-alkyl and
R32 is hydrogen, 1-7C-alkyl, 3-7C-cycloalkyl, hydroxy-1-4C-alkyl or 1-4C-alkoxy-1-4C-alkyl,
or where
R31 and R32 together, including the nitrogen atom to which both are bonded, are a pyrrolidino, hydroxypyrrolidino, aziridino, azetidino, piperidino, piperazino, N-1-4C-alkylpiperazino or morpholino group, X is O (oxygen) or NH and Ar is a mono- or bicyclic aromatic residue, substituted by R4, R5, R6 and R7, which is selected from the group consisting of phenyl, naphthyl, pyrrolyl, pyrazolyl, imidazolyl, 1,2,3-triazolyl, indolyl, benzimidazolyl, furyl, benzofuryl, thienyl, benzothienyl, thiazolyl, isoxazolyl, pyridinyl, pyrimidinyl, chinolinyl and isochinolinyl, wherein R4 is hydrogen, 1-4C-alkyl, hydroxy-1-4C-alkyl, 1-4C-alkoxy, 2-4C-alkenyloxy, 1-4C-alkylcarbonyl, carboxy, 1-4C-alkoxycarbonyl, carboxy-1-4C-alkyl, 1-4C-alkoxycarbonyl-1-4C-alkyl, halogen, hydroxy, aryl, aryl-1-4C-alkyl, aryl-oxy, aryl-1-4C-alkoxy, trifluoromethyl, nitro, amino, mono- or di-1-4C-alkylamino, 1-4C-alkylcarbonylamino, 1-AC-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen, trifluoromethyl or hydroxy, R6 is hydrogen, 1-4C-alkyl or halogen and R7 is hydrogen, 1-4C-alkyl or halogen, and wherein aryl is phenyl or substituted phenyl with one, two or three same or different substituents from the group of 1-4C-alkyl, 1-4C-alkoxy, carboxy, 1-4C-alkoxycarbonyl, halogen, trifluoromethyl, nitro, trifluoromethoxy, hydroxy and cyano, or a hydrate, solvate, salt, hydrate of a salt or solvate of a salt thereof.

2. A compound of formula 1 according to claim 1, in which

R1 is hydrogen, halogen, hydroxyl, 1-4C-alkyl, 3-7C-cycloalkyl, 3-7C-cycloalkyl-1-4C-alkyl, 1-4C-alkoxy, 1-4C-alkoxy-1-4C-alkyl, 1-4C-alkoxycarbonyl, 2-4C-alkenyl, 2-4C-alkynyl, fluoro-1-4C-alkyl, hydroxy-1-4C-alkyl or mono- or di-1-4C-alkylamino, R2 is hydrogen; 1-4C-alkyl, 1-4C-alkoxy, 1-4C-alkoxy-1-4C-alkyl, aryl, 3-7C-cycloalkyl, 3-7C-cycloalkyl-1-4C-alkyl, 1-4C-alkoxycarbonyl, mono- or di-1-4C-alkylamino-1-4C-alkylcarbonyl, hydroxy-1-4C-alkyl, fluoro-2-4C-alkyl, R3 is hydrogen, halogen, fluoro-1-4C-alkyl, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, fluoro-1-4C-alkoxy-1-4C-alkyl or the group —CO—NR31R32, where R31 is hydrogen, hydroxyl, 1-7C-alkyl, hydroxy-1-4C-alkyl or 1-4C-alkoxy-1-4C-alkyl and R32 is hydrogen, 1-7C-alkyl, hydroxy-1-4C-alkyl or 1-4C-alkoxy-1-4C-alkyl, or where R31 and R32 together, including the nitrogen atom to which both are bonded, are a pyrrolidino, piperidino, piperazino, N-1-4C-alkylpiperazino or morpholino group, X is 0 (oxygen) or NH and Ar is a mono- or bicyclic aromatic residue, substituted by R4, R5, R6 and R7, which is selected from the group consisting of phenyl, naphthyl, pyrrolyl, pyrazolyl, imidazolyl, 1,2,3-triazolyl, indolyl, benzimidazolyl, furyl, benzofuryl, thienyl, benzothienyl, thiazolyl, isoxazolyl, pyridinyl, pyrimidinyl, chinolinyl and isochinolinyl, wherein R4 is hydrogen, 1-4C-alkyl, hydroxy-1-4C-alkyl, 1-4C-alkoxy, 2-4C-alkenyloxy, 1-4C-alkylcarbonyl, carboxy, 1-4C-alkoxycarbonyl, carboxy-1-4C-alkyl, 1-4C-alkoxycarbonyl-1-4C-alkyl, halogen, hydroxy, aryl, aryl-1-4C-alkyl, aryl-oxy, aryl-1-4C-alkoxy, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen, trifluoromethyl or hydroxy, R6 is hydrogen, 1-4C-alkyl or halogen and R7 is hydrogen, 1-4C-alkyl or halogen, and wherein aryl is phenyl or substituted phenyl with one, two or three same or different substituents from the group of 1-4C-alkyl, 1-4C-alkoxy, carboxy, 1-4C-alkoxycarbonyl, halogen, trifluoromethyl, nitro, trifluoromethoxy, hydroxy and cyano, or a hydrate, solvate, salt, hydrate of a salt or solvate of a salt thereof.

3. A compound of formula 1 according to claim 1, in which

R1 is hydrogen, 1-4C-alkyl, 3-7C-cycloalkyl or fluoro-1-4C-alkyl,

R2 is hydrogen, 1-4C-alkyl or 1-4C-alkoxy-1-4C-alkyl,

R3 is hydrogen, halogen, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32, where R31 is hydrogen, 1-4C-alkyl, 3-7C-cycloalkyl, hydroxy-1-4C-alkyl or 1-4C-alkoxy-1-4C-alkyl and R32 is hydrogen or 1-4C-alkyl, or where R31 and R32 together, including the nitrogen atom to which both are bonded, are a pyrrolidino, hydroxy-pyrrolidino, aziridino, azetidino, piperidino, piperazino, N-1-4C-alkylpiperazino or morpholino group, X is 0 (oxygen) or NH and Ar is a phenyl group, substituted by R4, RS, RE and R7, wherein R4 is hydrogen, 1-4C-alkyl, hydroxy-1-4C-alkyl, 1-4C-alkoxy, 2-4C-alkenyloxy, 1-4C-alkylcarbonyl, carboxy, 1-4C-alkoxycarbonyl, carboxy-1-4C-alkyl, 1-4C-alkoxycarbonyl-1-4C-alkyl, halogen, hydroxy, trifluoromethyl, nitro, amino, mono- or di-1-4C-alkylamino, 1-4C-alkylcarbonylamino, 1-4C-alkoxycarbonylamino, 1-4C-alkoxy-1-4C-alkoxycarbonylamino or sulfonyl, R5 is hydrogen, 1-4C-alkyl, 1-4C-alkoxy, 1-4C-alkoxycarbonyl, halogen, trifluoromethyl or hydroxy, R6 is hydrogen, 1-4C-alkyl or halogen and R7 is hydrogen, 1-4C-alkyl or halogen, or a hydrate, solvate, salt, hydrate of a salt or solvate of a salt thereof.

4. A compound according to claim 1, characterized by the formula 1a,

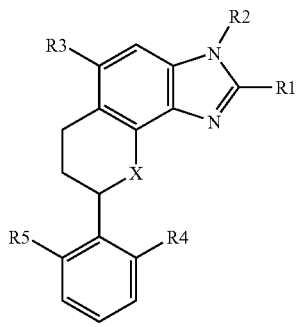

(1a)

in which
R1 is hydrogen, 1-4C-alkyl, 3-7C-cycloalkyl or fluoro-1-4C-alkyl,
R2 is hydrogen, 1-4C-alkyl or 1-4C-alkoxy-1-4C-alkyl,
R3 is hydrogen, halogen, carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32,
where
R31 is hydrogen, 1-4C-alkyl, 3-7C-cycloalkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a Pyrrolidino, hydroxypyrrolidino, aziridino, azetidino, piperidino, piperazino, N-1-4C-alkylpiperazino or morpholino group,
R4 is hydrogen, 1-4C-alkyl, hydroxy-1-4C-alkyl, 1-4C-alkoxy, 1-4C-alkoxycarbonyl, trifluoromethyl, amino, mono- or di-1-4C-alkylamino, l-4C-alkylcarbonylamino, 1-4C-alkoxycarbonylamino or 1-4C-alkoxy-1-4C-alkoxycarbonyl amino,
R5 is hydrogen, 1-4C-alkyl or 1-4C-alkoxy and
X is 0 (oxygen) or NH,
or a hydrate, solvate, salt, hydrate of a salt or solvate of a salt thereof.

5. A compound of formula 1a according to claim 4,
in which
R1 is 1-4C-alkyl, 3-7C-cycloalkyl or fluoro-1-4C-alkyl,
R2 is hydrogen, 1-4C-alkyl or 1-4C-alkoxy-1-4C-alkyl,
R3 is hydrogen, carboxyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32,
where
R31is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, aziridino, azetidino or morpholino group,
R4 is hydrogen,
R5 is hydrogen and
X is 0 (oxygen) or NH,
or a hydrate, solvate, salt, hydrate of a salt or solvate of a salt thereof.

6. A compound of formula 1a according to claim 4,
in which
R1 is 1-4C-alkyl, 3-7C-cycloalkyl or fluoro-1-4C-alkyl,
R2 is 1-4C-alkyl or 1-4C-alkoxy-1-4C-alkyl,
R3 is carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32,
where
R31 is hydrogen, 1-4C-alkyl, hydroxy-1-4C-alkyl or 1-4C-alkoxy 1-4C-alkyl and
R32 is hydrogen or 1-4C-alkyl,
or where
R31 and R32 together, including the nitrogen atom to which both are bonded, are a pyrrolidino, hydroxypyrrolidino, aziridino, azetidino or morpholino group,
R4 is hydrogen,
R5 is hydrogen and
X is 0 (oxygen) or NH,
or a hydrate, solvate, salt, hydrate of a salt or solvate of a salt thereof.

7. A compound of the formula 1a according to claim 4, in which
R1 is 1-4C-alkyl,
R2 is 1-4C-alkyl,
R3 is hydroxy-1-4C-alkyl, 1-4C-alkoxy-1-4C-alkyl or the group —CO—NR31R32,
where
R31 is hydrogen, 1-4C-alkyl, hydroxy-2-4C-alkyl or 1-4C-alkoxy 2-4C-alkyl and
R32 is hydrogen,
or where
R31 and R32 together, including the nitrogen atom to which both are bonded, are a pyrrolidino group,
R4 is hydrogen,
R5 is hydrogen and
X is 0 (oxygen) or NH,
or a hydrate, solvate, salt, hydrate of a salt or solvate of a salt thereof.

8. A compound of formula 1a according to claim 4,
in which
R1 is 1-4C-alkyl or fluoro-1-4C-alkyl,
R2 is 1-4C-alkyl or 1-4C-alkoxy-1-4C-alkyl,
R3 is carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl or the group —CO—NR31R32,
where
R31 is hydrogen, 1-4C-alkyl, hydroxy-2-4C-alkyl or 1-4C-alkoxy-2-4C-alkyl and
R32 is hydrogen or 1-4C-alkyl,
or where
R3l and R32 together, including the nitrogen atom to which both are bonded, are a pyrrolidino or morpholino group,
R4 is hydrogen,
R5 is hydrogen and
X is 0 (oxygen) or NH,
or a hydrate, solvate, salt, hydrate of a salt or solvate of a salt thereof.

9. A compound according to claim 1, characterized by the formula 2,

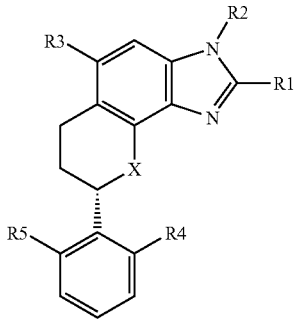

(2)

in which
R1 is 1-4C-alkyl or 3-7C-cycloalkyl,
R2 is hydrogen or 1-4C-alkyl,
R3 is 1-4C-alkoxycarbonyl, hydroxy-1-4C-alkyl, 1-4C-alkoxy-1-4C-alkyl or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a. pyrrolidino, aziridino, azetidino or morpholino group,
R4 is hydrogen,
R5 is hydrogen and
X is O (oxygen) or NH,
or a hydrate, solvate, salt, hydrate of a salt or solvate of a salt thereof.

10. A compound of formula 2 according to claim 9, in which
R1 is 1-4C-alkyl, 3-7C-cycloalkyl or fluoro-1-4C-alkyl,
R2 is 1-4C-alkyl or 1-4C-alkoxy-1-4C-alkyl,
R3 is carboxyl, 1-4C-alkoxycarbonyl, hydroxy-1-4C-alkyl, 1-4C-alkoxy-1-4C-alkyl, 1-4C-alkoxy-1-4C-alkoxy-1-4C-alkyl, 1-4C-alkylcarbonyl-N-1-4C-alkylamino or the group —CO—NR31R32,
where
R31 is hydrogen, 1-4C-alkyl, hydroxy-1-4C-alkyl or 1-4C-alkoxy-1-4C-alkyl and
R32 is hydrogen or 1-4C-alkyl,
or where
R31 and R32 together, including the nitrogen atom to which both are bonded, are a pyrrolidino, hydroxy-pyrrolidino, aziridino, azetidino or morpholino group,
R4 is hydrogen,
R5 is hydrogen and
X is O (oxygen) or NH,
or a hydrate, solvate, salt, hydrate of a salt or solvate of a salt thereof.

11. A pharmaceutical composition comprising a compound as claimed in claim 1 and/or a pharmacologically acceptable hydrate, solvate, salt, hydrate of a salt or solvate of a salt thereof together with a pharmaceutically acceptable auxiliary and/or excipient.

12. A method of treating a gastrointestinal disorder in a patient comprising administering to a patient in need thereof a therapeutically effective amount of a compound as claimed in claim 1 or a hydrate, solvate, salt, hydrate of a salt or solvate of a salt thereof.

13. A compound of formula 1 according to claim 1 selected from the group consisting of (8S)-2,3-dimethyl-8-phenyl-3,6,7,8-tetrahydro-chromeno[7,8-d]imidazole-5-carboxylic acid dimethylamide, (8S)-2-methyl-8-phenyl-3,6,7,8-tetrahydro-chromeno[7,8-d]imidazole-5-carboxylic acid dimethylamide oxalate, and (8S)-2,3-dimethyl-8-phenyl-3,6,7,8-tetrahydro-chromenol[7,8-d]imidazole-5-carboxylic acid methylamide.

14. A compound of the general formula 2,

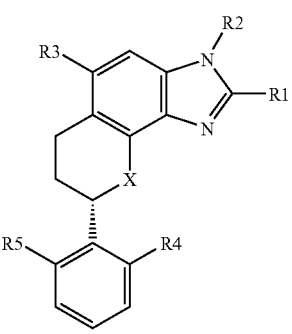

(2)

in which the substituents R1, R2, R3, R4, R5 and X have the meanings given in the following table, whereby Me is CH3 and Et is C2H5

TABLE 1

| R1 | R2 | R3 | R4 | R5 | X |
|---|---|---|---|---|---|
| Me | Me | CH$_2$OH | H | H | O |
| Me | Me | CH$_2$OCH$_3$ | H | H | O |
| Me | Me | CONHMe | H | H | O |
| Me | Me | CON-pyrrolidine | H | H | O |
| Me | Me | CONH(CH$_2$)$_2$OH | H | H | O |
| Me | Me | CONH(CH$_2$)$_2$OMe | H | H | O |
| Me | Me | CONH$_2$ | H | H | O |
| Me | Me | CON-morpholine | H | H | O |
| Me | Me | CONMe$_2$ | H | H | O |
| Me | Me | CH$_2$O(CH$_2$)$_2$OMe | H | H | O |
| Me | Me | CON-aziridine | H | H | O |
| Me | Me | COOEt | H | H | O |
| Me | Me | COOH | H | H | O |
| Me | Me | CON-azetidine | H | H | O |
| Me | Me | CONH(CH$_2$)$_2$Me | H | H | O |
| Me | Me | CONHCH$_2$CHOHCH$_2$OH | H | H | O |
| Me | Me | NCH$_3$COCH$_3$ | H | H | O |
| Me | Me | NHCOCH$_3$ | H | H | O |
| Me | Me | NHCOCH$_2$OMe | H | H | O |
| Me | Me | NHCO(CH$_2$)$_2$OMe | H | H | O |
| Me | Me | OCH$_2$OMe | H | H | O |
| Me | Me | O(CH$_2$)$_2$OMe | H | H | O |
| Me | Me | CONH-cyclopropyl | H | H | O |
| Me | Me | H | H | H | O |
| Cyclopropyl | Me | CH$_2$OCH$_3$ | H | H | O |
| Cyclopropyl | Me | CONHMe | H | H | O |
| Cyclopropyl | Me | CON-pyrrolidine | H | H | O |
| Cyclopropyl | Me | CONH(CH$_2$)$_2$OH | H | H | O |
| Cyclopropyl | Me | CONH(CH$_2$)$_2$OMe | H | H | O |
| Cyclopropyl | Me | CONH$_2$ | H | H | O |
| Cyclopropyl | Me | CON-morpholine | H | H | O |
| Cyclopropyl | Me | CONMe$_2$ | H | H | O |
| Cyclopropyl | Me | CH$_2$O(CH$_2$)$_2$OMe | H | H | O |
| Cyclopropyl | Me | CON-aziridine | H | H | O |
| Cyclopropyl | Me | COOEt | H | H | O |
| Cyclopropyl | Me | COOH | H | H | O |
| Cyclopropyl | Me | CON-azetidine | H | H | O |

TABLE 1-continued

| R1 | R2 | R3 | R4 | R5 | X |
|---|---|---|---|---|---|
| Cyclopropyl | Me | CONH(CH₂)₂Me | H | H | O |
| Cyclopropyl | Me | CONHCH₂CHOHCH₂OH | H | H | O |
| Cyclopropyl | Me | NCH₃COCH₃ | H | H | O |
| Cyclopropyl | Me | NHCOCH₃ | H | H | O |
| Cyclopropyl | Me | NHCOCH₂OMe | H | H | O |
| Cyclopropyl | Me | NHCO(CH₂)₂OMe | H | H | O |
| Cyclopropyl | Me | OCH₂OMe | H | H | O |
| Cyclopropyl | Me | O(CH₂)₂OMe | H | H | O |
| Cyclopropyl | Me | CONH-cyclopropyl | H | H | O |
| Cyclopropyl | Me | H | H | H | O |
| CF₃ | Me | CH₂OCH₃ | H | H | O |
| CF₃ | Me | CONHMe | H | H | O |
| CF₃ | Me | CON-pyrrolidine | H | H | O |
| CF₃ | Me | CONH(CH₂)₂OH | H | H | O |
| CF₃ | Me | CONH(CH₂)₂OMe | H | H | O |
| CF₃ | Me | CONH₂ | H | H | O |
| CF₃ | Me | CON-morpholine | H | H | O |
| CF₃ | Me | CONMe₂ | H | H | O |
| CF₃ | Me | CH₂O(CH₂)₂OMe | H | H | O |
| CF₃ | Me | CON-aziridine | H | H | O |
| CF₃ | Me | COOEt | H | H | O |
| CF₃ | Me | COOH | H | H | O |
| CF₃ | Me | CON-azetidine | H | H | O |
| CF₃ | Me | CONH(CH₂)₂Me | H | H | O |
| CF₃ | Me | CONHCH₂CHOHCH₂OH | H | H | O |
| CF₃ | Me | NCH₃COCH₃ | H | H | O |
| CF₃ | Me | NHCOCH₃ | H | H | O |
| CF₃ | Me | NHCOCH₂OMe | H | H | O |
| CF₃ | Me | NHCO(CH₂)₂OMe | H | H | O |
| CF₃ | Me | OCH₂OMe | H | H | O |
| CF₃ | Me | O(CH₂)₂OMe | H | H | O |
| CF₃ | Me | CONH-cyclopropyl | H | H | O |
| CF₃ | Me | H | H | H | O |
| Me | CH₂OMe | CH₂OCH₃ | H | H | O |
| Me | CH₂OMe | CONHMe | H | H | O |
| Me | CH₂OMe | CON-pyrrolidine | H | H | O |
| Me | CH₂OMe | CONH(CH₂)₂OH | H | H | O |
| Me | CH₂OMe | CONH(CH₂)₂OMe | H | H | O |
| Me | CH₂OMe | CONH₂ | H | H | O |
| Me | CH₂OMe | CON-morpholine | H | H | O |
| Me | CH₂OMe | CONMe₂ | H | H | O |
| Me | CH₂OMe | CH₂O(CH₂)₂OMe | H | H | O |
| Me | CH₂OMe | CON-aziridine | H | H | O |
| Me | CH₂OMe | COOEt | H | H | O |
| Me | CH₂OMe | COOH | H | H | O |
| Me | CH₂OMe | CON-azetidine | H | H | O |
| Me | CH₂OMe | CONH(CH₂)₂Me | H | H | O |
| Me | CH₂OMe | CONHCH₂CHOHCH₂OH | H | H | O |
| Me | CH₂OMe | NCH₃COCH₃ | H | H | O |
| Me | CH₂OMe | NHCOCH₃ | H | H | O |
| Me | CH₂OMe | NHCOCH₂OMe | H | H | O |
| Me | CH₂OMe | NHCO(CH₂)₂OMe | H | H | O |
| Me | CH₂OMe | OCH₂OMe | H | H | O |
| Me | CH₂OMe | O(CH₂)₂OMe | H | H | O |
| Me | CH₂OMe | CONH-cyclopropyl | H | H | O |
| Me | CH₂OMe | H | H | H | O |
| Me | H | CH₂OCH₃ | H | H | O |
| Me | H | CONHMe | H | H | O |
| Me | H | CON-pyrrolidine | H | H | O |
| Me | H | CONH(CH₂)₂OH | H | H | O |
| Me | H | CONH(CH₂)₂OMe | H | H | O |
| Me | H | CONH₂ | H | H | O |
| Me | H | CON-morpholine | H | H | O |
| Me | H | CONMe₂ | H | H | O |
| Me | H | CH₂O(CH₂)₂OMe | H | H | O |
| Me | H | CON-aziridine | H | H | O |
| Me | H | COOEt | H | H | O |
| Me | H | COOH | H | H | O |
| Me | H | CON-azetidine | H | H | O |
| Me | H | CONH(CH₂)₂Me | H | H | O |
| Me | H | CONHCH₂CHOHCH₂OH | H | H | O |
| Me | H | NCH₃COCH₃ | H | H | O |
| Me | H | NHCOCH₃ | H | H | O |
| Me | H | NHCOCH₂OMe | H | H | O |
| Me | H | NHCO(CH₂)₂OMe | H | H | O |
| Me | H | OCH₂OMe | H | H | O |
| Me | H | O(CH₂)₂OMe | H | H | O |
| Me | H | CONH-cyclopropyl | H | H | O |
| Me | H | H | H | H | O |
| Me | Me | H | H | H | NH |
| Cyclopropyl | Me | CH₂OCH₃ | H | H | NH |
| Cyclopropyl | Me | CONHMe | H | H | NH |
| Cyclopropyl | Me | CON-pyrrolidine | H | H | NH |
| Cyclopropyl | Me | CONH(CH₂)₂OH | H | H | NH |
| Cyclopropyl | Me | CONH(CH₂)₂OMe | H | H | NH |
| Cyclopropyl | Me | CONH₂ | H | H | NH |
| Cyclopropyl | Me | CON-morpholine | H | H | NH |
| Cyclopropyl | Me | CONMe₂ | H | H | NH |
| Cyclopropyl | Me | CH₂O(CH₂)₂OMe | H | H | NH |
| Cyclopropyl | Me | CON-aziridine | H | H | NH |
| Cyclopropyl | Me | COOEt | H | H | NH |
| Cyclopropyl | Me | COOH | H | H | NH |
| Cyclopropyl | Me | CON-azetidine | H | H | NH |
| Cyclopropyl | Me | CONH(CH₂)₂Me | H | H | NH |
| Cyclopropyl | Me | CONHCH₂CHOHCH₂OH | H | H | NH |
| Cyclopropyl | Me | NCH₃COCH₃ | H | H | NH |
| Cyclopropyl | Me | NHCOCH₃ | H | H | NH |
| Cyclopropyl | Me | NHCOCH₂OMe | H | H | NH |
| Cyclopropyl | Me | NHCO(CH₂)₂OMe | H | H | NH |
| Cyclopropyl | Me | OCH₂OMe | H | H | NH |
| Cyclopropyl | Me | O(CH₂)₂OMe | H | H | NH |
| Cyclopropyl | Me | CONH-cyclopropyl | H | H | NH |
| Cyclopropyl | Me | H | H | H | NH |
| CF₃ | Me | CH₂OCH₃ | H | H | NH |
| CF₃ | Me | CONHMe | H | H | NH |
| CF₃ | Me | CON-pyrrolidine | H | H | NH |
| CF₃ | Me | CONH(CH₂)₂OH | H | H | NH |
| CF₃ | Me | CONH(CH₂)₂OMe | H | H | NH |
| CF₃ | Me | CONH₂ | H | H | NH |
| CF₃ | Me | CON-morpholine | H | H | NH |
| CF₃ | Me | CONMe₂ | H | H | NH |
| CF₃ | Me | CH₂O(CH₂)₂OMe | H | H | NH |
| CF₃ | Me | CON-aziridine | H | H | NH |
| CF₃ | Me | COOEt | H | H | NH |
| CF₃ | Me | COOH | H | H | NH |
| CF₃ | Me | CON-azetidine | H | H | NH |
| CF₃ | Me | CONH(CH₂)₂Me | H | H | NH |
| CF₃ | Me | CONHCH₂CHOHCH₂OH | H | H | NH |
| CF₃ | Me | NCH₃COCH₃ | H | H | NH |
| CF₃ | Me | NHCOCH₃ | H | H | NH |
| CF₃ | Me | NHCOCH₂OMe | H | H | NH |
| CF₃ | Me | NHCO(CH₂)₂OMe | H | H | NH |
| CF₃ | Me | OCH₂OMe | H | H | NH |
| CF₃ | Me | O(CH₂)₂OMe | H | H | NH |
| CF₃ | Me | CONH-cyclopropyl | H | H | NH |
| CF₃ | Me | H | H | H | NH |
| Me | CH₂OMe | CH₂OCH₃ | H | H | NH |
| Me | CH₂OMe | CONHMe | H | H | NH |
| Me | CH₂OMe | CON-pyrrolidine | H | H | NH |
| Me | CH₂OMe | CONH(CH₂)₂OH | H | H | NH |
| Me | CH₂OMe | CONH(CH₂)₂OMe | H | H | NH |
| Me | CH₂OMe | CONH₂ | H | H | NH |
| Me | CH₂OMe | CON-morpholine | H | H | NH |
| Me | CH₂OMe | CONMe₂ | H | H | NH |
| Me | CH₂OMe | CH₂O(CH₂)₂OMe | H | H | NH |
| Me | CH₂OMe | CON-aziridine | H | H | NH |
| Me | CH₂OMe | COOEt | H | H | NH |
| Me | CH₂OMe | COOH | H | H | NH |
| Me | CH₂OMe | CON-azetidine | H | H | NH |
| Me | CH₂OMe | CONH(CH₂)₂Me | H | H | NH |
| Me | CH₂OMe | CONHCH₂CHOHCH₂OH | H | H | NH |
| Me | CH₂OMe | NCH₃COCH₃ | H | H | NH |
| Me | CH₂OMe | NHCOCH₃ | H | H | NH |
| Me | CH₂OMe | NHCOCH₂OMe | H | H | NH |
| Me | CH₂OMe | NHCO(CH₂)₂OMe | H | H | NH |
| Me | CH₂OMe | OCH₂OMe | H | H | NH |
| Me | CH₂OMe | O(CH₂)₂OMe | H | H | NH |
| Me | CH₂OMe | CONH-cyclopropyl | H | H | NH |
| Me | CH₂OMe | H | H | H | NH |
| Me | H | CH₂OCH₃ | H | H | NH |
| Me | H | CONHMe | H | H | NH |
| Me | H | CON-pyrrolidine | H | H | NH |
| Me | H | CONH(CH₂)₂OH | H | H | NH |
| Me | H | CONH(CH₂)₂OMe | H | H | NH |

TABLE 1-continued

| R1 | R2 | R3 | R4 | R5 | X |
|---|---|---|---|---|---|
| Me | H | CONH$_2$ | H | H | NH |
| Me | H | CON-morpholine | H | H | NH |
| Me | H | CONMe$_2$ | H | H | NH |
| Me | H | CH$_2$O(CH$_2$)$_2$OMe | H | H | NH |
| Me | H | CON-aziridine | H | H | NH |
| Me | H | COOEt | H | H | NH |
| Me | H | COOH | H | H | NH |
| Me | H | CON-azetidine | H | H | NH |
| Me | H | CONH(CH$_2$)$_2$Me | H | H | NH |
| Me | H | CONHCH$_2$CHOHCH$_2$OH | H | H | NH |
| Me | H | NCH$_3$COCH$_3$ | H | H | NH |
| Me | H | NHCOCH$_3$ | H | H | NH |
| Me | H | NHCOCH$_2$OMe | H | H | NH |
| Me | H | NHCO(CH$_2$)$_2$OMe | H | H | NH |
| Me | H | OCH$_2$OMe | H | H | NH |
| Me | H | O(CH$_2$)$_2$OMe | H | H | NH |
| Me | H | CONH-cyclopropyl | H | H | NH |
| Me | H | H | H | H | NH | or a hydrate, solvate, salt, hydrate of a salt or solvate of a salt thereof.

15. A compound according to claim 1 which is selected from the group consisting of 2,3-Dimethyl-8-phenyl-3,6,7,8-tetrahydro-chromeno[7,8-a]imidazole-5-carboxylic acid dimethylamide, 2,3-Dimethyl-8-phenyl-6,7,8,9-tetrahydro-3H-imidazo[4,5-h]quinoline-5-carboxylic acid dimethylamide, 2,3-Dimethyl-8-phenyl-3,6,7,8-tetrahydro-chromeno[7,8-d]imidazole-5-carboxylic acid amide, 2,3-Dimethyl-8-phenyl-3,6,7,8-tetrahydro-chromeno[7,8-d]imidazole-5-carboxylic acid methylamide, 2,3-Dimethyl-8-phenyl-3,6,7,8-tetrahydro-chromeno[7,8-d]imidazole-5-carboxylic acid (2-hydroxy-ethyl)-amide, 2,3-Dimethyl-8-phenyl-3,6,7,8-tetrahydro-chromeno[7,8-d]imidazole-5-carboxylic acid (2-methoxy-ethyl)-amide, 1-(2,3-Dirnethyl-8-phenyl-3,6,7,8-tetrahydro-chromeno[7,8-d]imidazol-5-yl)-1-morpholin-4-yl-methanone, 1-(2,3-Dimethyl-8-phenyl-3,6,7,8-tetrahydro-chromeno[7,8-d]imidazol-5-yl)-1-pyrrolidin.-1-yl-methanone, 2-Isopropyl-3-methyl-8-phenyl-3,6,7,8-tetrahydro-chromenol [7,8-d]imidazole-5-carboxylic acid dimethylamide, 2-Cyclopropyl-3-methyl-8-phenyl-3,6,7,8-tetrahydro-chromeno [7,8-d]imidazole-5-carboxylic acid dimethylamide, 5-Methoxymethyl-2,3-dimethyl-8-phenyl-3,6,7,8-tetrahydro-chromeno [7,8-d]imidazole oxalic acid, 5-(2-Methoxy-ethoxyrnethyl)-2,3-dimethyl-8-phenyl-3,6,7,8-tetrahydro-chromeno [7,8-d]-imidazole oxalic acid, 1-Aziridin-1-yl-1-(2,3-dimethyl-8-phenyl-3,6,7,8-tetrahydro-chromeno [7,8-d]imidazol-5-yl)-methanone, 3-Methyl-8-phenyl-2-trifluoromethyl-3,6,7,8-tetrahydro-chromenol [7,8-d]imidazole-5-carboxylic acid dimethylamide, 2,3-Dimethyl-8-pheriyl-3,6,7,8-tetrahydro-chromeno[7,8-d]imidazole-5-carboxylic acid ethyl ester, 2,3-Dimethyl-8-phenyl-3,6,7,8-tetrahydro-chromeno[7,8-d]imidazole-5-carboxylic acid, (2,3-Dimethyl-8-phenyl-3,6,7,8-tetrahydro-chromeno[7,8-d]imidazol-5-yl)-methanol, 1-Azetidin-1-yl-1-(2,3-dimethyl-8-phenyl-3,6,7,8-tetrahydro-chromeno [7,8-d]imidazol-5-yl)-methanone, 2,3-Dimethyl-8-phenyl-3,6,7,8-tetrahydro-chromeno[7,8-d]imidazole-5-carboxylic acid propyl-amide, 1-(2,3-Dimethyl-8-phenyl-3,6,7,8-tetrahydro-chromeno [7,8-d]imidazol-5-yl)-1-(3-hydroxy-pyrrolidin-1-yl)-methanone, 2,3-Dimethyl-8-phenyl-3,6,7,8-tetrahydro-chromeno[7,8-d]imidazole-5-carboxylic acid (2,3-dihydroxy-propyl)-amide, 3-Methoxymethyl-2-methyl-8-phenyl-3,6,7,8-tetrahydrochromeno [7,8-d]imidazole-5-carboxylic Acid Dimethylamide, N-(2,3-Dimethyl-8-phenyl-3,6,7,8-tetrahydro-chromeno[7,8-d]imidazol-5-yl)-N-methyl-acetamide, 2-Ethyl-3-methyl-8-phenyl-3,6,7,8-tetrahydro-chromeno [7,8-d]imidazole-5-carboxylic acid dimethylamide, Ethyl 2,3-dimethyl-8-phenyl-6,7,8,9-tetrahydro-3H-imidazo [4,5-h]quirioline-5-carboxylate, 2,3-Dimethyl-8-phenyl-6,7,8,9-tetrahydro-3H-imidazo[4,5-h]quinoline-5-carboxylic acid, 2,3-Dimethyl-8-phenyl-6,7,8,9-tetrahydro-3H-imidazo[4,5-h]quinoline-5-carboxylic acid 2-hydroxy-ethylamide, 2,3-Dimethyl-8-phenyl-6,7,8,9-tetrahydro-3H-imidazo[4,5-h]quinoline-5-carboxylic acid amide, 2,3-Dimethyl-8-phenyl-6,7,8,9-tetrahydro-3H-imidazo[4,5-h]quinoline-5-carboxylic acid methylamide, 2,3-Dimethyl-8-phenyl-6,7,8,9-tetrahydro-3H-imidazo[4,5-h]quinoline-5-carboxylic acid 1-aziridinyl-amide, 5-Hydroxymethyl-2,3-dimethyl-8-phenyl-6,7,8,9-tetrahydro-3H-imidazo [4,5-h]quinolirie, (8S)- and (BR)-2,3-Dimethyl-8-phenyl-G,7,8,9-tetrahydro-3H-imidazo [4,5-h]quinoline-5-carboxylic acid methylamide, (8S)-2,3-Dimethyl-8-phenyl-3,6,7,8-tetrahydro-chromeno [7,8-d]imidazole-5-carboxylic acid dimethylarnide, (8R)-2,3-Dimethyl-8-phenyl-3,6,7,8-tetrahydro-chromeno [7,8-d]imidazole-5-carboxylic acid dimethylamide, 2,3-Dimethyl-8-phenyl-3,6,7,8-tetrahydro-chromeno [7,8-d]imidazole-5-carboxylic acid cyclopropyl-amide, 2,3-Dimethyl-8-phenyl-3,6,7,8-tetrahydro-chromeno [7,8-d]imidazole, 2-Methyl-8-phenyl-3,6,7,8-tetrahydro-chromeno [7,8-d]imidazole-5-carboxylic acid dimethylamide, (S)-2,3-Dimethyl-8-phenyl-3,6,7,8-tetrahydro-chromeno [7,8-d]imidazole-5-carboxylic acid dimethylamide, and the hydrates, solvates, salts, hydrates of the salts and solvates of the salts thereof.

* * * * *

UNITED STATES PATENT AND TRADEMARK OFFICE
CERTIFICATE OF CORRECTION

| | |
|---|---|
| PATENT NO. | : 7,307,084 B2 |
| APPLICATION NO. | : 10/551049 |
| DATED | : December 11, 2007 |
| INVENTOR(S) | : Buhr et al. |

It is certified that error appears in the above-identified patent and that said Letters Patent is hereby corrected as shown below:

Claim 1, Column 44, Line 40,
Please delete "Rb 1"
and
replace with
-- R1 --

Claim 1, Column 44, Line 54,
Please delete "1-4C-alkylcarbonyamino,"
and
replace with
-- 1-4C-alkylcarbonylamino, --

Claim 1, Column 45, Lines 16-17,
Please delete "1-AC-alkoxylcarbonylamino,"
and
replace with
-- 1-4C-alkoxylcarbonylamino, --

Claim 3, Column 46, Line 47,
Please delete "X is 0 (oxygen)"
and
replace with
-- X is O (oxygen) --

Claim 3, Column 46, Line 48,
Please delete "R4, RS, RE and R7,"
and
replace with
-- R4, R5, R6 and R7, --

Claim 4, Column 47, Line 34,
Please delete "Pyrrolidino"
and
replace with
-- pyrrolidino --

UNITED STATES PATENT AND TRADEMARK OFFICE
CERTIFICATE OF CORRECTION

PATENT NO.      : 7,307,084 B2
APPLICATION NO. : 10/551049
DATED           : December 11, 2007
INVENTOR(S)     : Buhr et al.

It is certified that error appears in the above-identified patent and that said Letters Patent is hereby corrected as shown below:

Claim 4, Column 47, Line 43,
Please delete "X is 0 (oxygen)"
and
replace with
-- X is O (oxygen) --

Claim 5, Column 47, Line 65,
Please delete "X is 0 (oxygen)"
and
replace with
-- X is O (oxygen) --

Claim 6, Column 48, Line 12,
Please delete "1-4C-alkoxy 1-4C-alkyl and"
and
replace with
-- 1-4C-alkoxy-1-4C-alkyl and --

Claim 6, Column 48, Line 22,
Please delete "X is 0 (oxygen)"
and
replace with
-- X is O (oxygen) --

Claim 7, Column 48, Line 43,
Please delete "X is 0 (oxygen)"
and
replace with
-- X is O (oxygen) --

Claim 8, Column 48, Line 65,
Please delete "X is 0 (oxygen)"
and
replace with
-- X is O (oxygen) --

UNITED STATES PATENT AND TRADEMARK OFFICE
CERTIFICATE OF CORRECTION

PATENT NO.       : 7,307,084 B2
APPLICATION NO.  : 10/551049
DATED            : December 11, 2007
INVENTOR(S)      : Buhr et al.

It is certified that error appears in the above-identified patent and that said Letters Patent is hereby corrected as shown below:

Claim 9, Column 49, Line 31,
Please delete "are a. pyrrolidino,"
and
replace with
-- are a pyrrolidino, --

Claim 9, Column 49, Line 35,
Please delete "X is 0 (oxygen)"
and
replace with
-- X is O (oxygen) --

Claim 10, Column 49, Line 58,
Please delete "X is 0 (oxygen)"
and
replace with
-- X is O (oxygen) --

Claim 14, Column 50, Lines 31-32,
Please delete "Me is CH3 and Et is C2H$_5$"
and
replace with
-- Me is CH$_3$ and Et is C$_2$H$_5$ --

Claim 15, Column 53, Line 45,
Please delete "chromenol"
and
replace with
-- chromeno --

Claim 15, Column 53, Line 59,
Please delete "chromenol"
and
replace with
-- chromeno --

UNITED STATES PATENT AND TRADEMARK OFFICE
CERTIFICATE OF CORRECTION

| | |
|---|---|
| PATENT NO. | : 7,307,084 B2 |
| APPLICATION NO. | : 10/551049 |
| DATED | : December 11, 2007 |
| INVENTOR(S) | : Buhr et al. |

It is certified that error appears in the above-identified patent and that said Letters Patent is hereby corrected as shown below:

Claim 15, Column 54, Line 1,
Please delete "pheriyl"
and
replace with
-- phenyl --

Claim 15, Column 54, Line 25,
Please delete "quirioline"
and
replace with
-- quinoline --

Claim 15, Column 54, Line 39,
Please delete "quinolirie"
and
replace with
-- quinoline --

Claim 15, Column 54, Line 40,
Please delete "(BR)"
and
replace with
-- (8R) --

Claim 15, Column 54, Line 40,
Please delete "8-phenyl-G,7,8,9"
and
replace with
-- 8-phenyl-6,7,8,9 --

UNITED STATES PATENT AND TRADEMARK OFFICE
CERTIFICATE OF CORRECTION

PATENT NO.      : 7,307,084 B2
APPLICATION NO. : 10/551049
DATED           : December 11, 2007
INVENTOR(S)     : Buhr et al.

It is certified that error appears in the above-identified patent and that said Letters Patent is hereby corrected as shown below:

Claim 15, Column 54, Lines 44-45,
Please delete "dimethy-larnide"
and
replace with
-- dimethyl-amide --

Signed and Sealed this

Second Day of June, 2009

JOHN DOLL
*Acting Director of the United States Patent and Trademark Office*